US010035871B2

(12) United States Patent
Langer et al.

(10) Patent No.: US 10,035,871 B2
(45) Date of Patent: Jul. 31, 2018

(54) URETHANE-CROSSLINKED BIODEGRADABLE ELASTOMERS

(75) Inventors: Robert S. Langer, Newton, MA (US); Jeffrey M. Karp, Brookline, MA (US); Maria Jose Maio Nunes-Pereira, Cambridge, MA (US); Ben Ouyang, Bedford, MA (US); Lino Da Silva Ferreira, Coimbra (PT); Debanjan Sarkar, Williamsville, NY (US)

(73) Assignees: Massachusetts Institute of Technology, Cambridge, MA (US); The Brigham and Women's Hospital, Inc., Boston, MA (US); Biocant-Center of Innovation and Biotechnology, Cantanhede (PT)

( * ) Notice: Subject to any disclaimer, the term of this patent is extended or adjusted under 35 U.S.C. 154(b) by 336 days.

(21) Appl. No.: 13/594,834

(22) Filed: Aug. 26, 2012

(65) Prior Publication Data

US 2013/0231412 A1    Sep. 5, 2013

Related U.S. Application Data

(60) Provisional application No. 61/527,879, filed on Aug. 26, 2011.

(51) Int. Cl.
*C08G 18/42*    (2006.01)
*C08G 18/08*    (2006.01)

(52) U.S. Cl.
CPC ......... *C08G 18/4236* (2013.01); *C08G 18/14* (2013.01); *C08G 18/4238* (2013.01); *C08G 18/4283* (2013.01)

(58) Field of Classification Search
CPC  C08G 18/14; C08G 18/4236; C08G 18/4283; C08G 18/4238
See application file for complete search history.

(56) References Cited

U.S. PATENT DOCUMENTS

| 7,722,894 | B2 | 5/2010 | Wang et al. | |
| 7,923,486 | B2 | 4/2011 | Yang et al. | |
| 8,143,042 | B2 | 3/2012 | Bettinger et al. | |
| 2009/0093565 | A1 * | 4/2009 | Yang et al. | 523/113 |
| 2010/0055184 | A1 | 3/2010 | Zeitels et al. | |
| 2010/0247600 | A1 | 9/2010 | Xia et al. | |
| 2011/0008277 | A1 | 1/2011 | Bruggeman et al. | |
| 2012/0269761 | A1 | 10/2012 | Bettinger et al. | |

FOREIGN PATENT DOCUMENTS

WO    WO 2007/107210 A1 *  9/2007
WO    WO 2008/144514 A2 *  11/2008

OTHER PUBLICATIONS

Szycher, Michael; Szycher's Handbook of Polyurethanes; CRC Press; New York; 1999; pp. 3-4-3-9.*
Cheng et al., A Novel Family of Biodegradable Poly(ester amide) Elastomers, Advanced Materials, 23; H95-H100 (2011).
Dey et al., Development of Biodegradable Crosslinked Urethane-Doped Polyester Elastomers, Biomaterials, 29(35); 4637-4649, 2008.
Liu et al., Sythesis, Preparation, in Vitro Degradation, and Application of novel degradable biolestomers—A review, Progress in Polymer Science, 37; 715-765 (2012).
Pereira et al., Presentation of Novel Generation of Biodegradable Elastomers with Highly Tunable Mechanical and Degradation Properties, American Chemical Society National Meeting, Boston (Aug. 26, 2010).
Bettinger et al., Amino alcohol-based degradable poly(ester amide) elastomers, Biomaterials, 29: 2315-2325 (2008).
Bouten, et al., Substrates for cardiovascular tissue engineering, Advanced drug delivery reviews, 63: 221-241 (2011).
Bruggeman et al., Biodegradable Xylitol-Based Polymers, Advanced Materials, 20: 1922-1927 (2008).
Chen et al., Characterisation of a soft elastomer ply(glycerol sebacate) designed to match the mechanical properties of myocardial tissue, Biomaterials, 29: 47-57 (2008).
Chen et al., An elastomeric patch derived from poly(glycerol sebacate) for delivery of embryonic stem cells to the heart, Biomaterials, 31: 3885-3893 (2010).
Fujimoto et al., In Vivo Evaluation of a Porous, Elastic, Biodegradable Patch for Reconstructive Cardiac Procedures, The Annals of thoracic surgery, 83: 648-654 (2007).
Fujimoto et al., An Elastic, Biodegradable Cardiac Patch Induces Contractile Smooth Muscle and Improves Cardiac Remodeling and Function in Subacute Myocardial Infarction, Journal of the American College of Cardiology, 49(23): 2292-2300 (2007).
Guan et al., Biodegradable poly(ether ester urethane)urea elastomers based on poly(ether ester) triblock copolymers and putrescine: synthesis, characterization and cytocompatibility, Biomaterials 25: 85-96 (2004).
Guelcher et al., Synthesis and In Vitro Biocompatibility of Injectable Polyurethane Foam Scaffolds, Tissue Engineering 12(5): 1247-1259 (2006).
Guelcher et al., Synthesis, In Vitro Degradation, and Mechanical Properties of Two-Component Poly(Ester Urethane)Urea Scaffolds: Effects of Water and Polyol Composition, Tissue Engineering, 13(9): 2321-2333 (2007).
Guelcher, Biodegradable Polyurethanes: Synthesis and Applications in Regenerative Medicine, Tissue Engineering Part B, 14(1): 3-17 (2008).
Li et al., The effect of the local delivery of platelet-derived growth factor from reactive two-component polyurethane scaffolds on the healing in rat skin excisional wounds, Biomaterials, 30: 3486-3494 (2009).
Liang et al., The mechanical characteristics and in vitro biocompatibility of poly(glycerol sebacate)-Bioglass elastomeric composites, Biomaterials, 31: 8516-8529 (2010).
Mainil-Varlet et al., Long-term soft tissue reaction to various polylactides and their in vivo degradation, Journal of Materials Science: Materials in Medicine, 7: 713-721 (1996).

(Continued)

*Primary Examiner* — Rabon Sergent
(74) *Attorney, Agent, or Firm* — Pabst Patent Group LLP

(57) ABSTRACT

Among other things, the present disclosure provides compositions and methods for an elastomeric cross-linked polyester material. Such an elastomeric cross-linked polyester material, in some embodiments, comprises a plurality of polymeric units of the general formula (-A-B—)$_p$, wherein p is an integer greater than 1; and a plurality of urethane cross-links each of which covalently links two polymeric units to one another, which two linked polymeric unit each had at least one free hydroxyl or amino group prior to formation of the crosslink.

20 Claims, 8 Drawing Sheets

(56) References Cited

OTHER PUBLICATIONS

Nijst et al., Synthesis and Characterization of Photocuable Elastomers from Poly(glycerol-co-sebacate), Biomacromolecules, 8: 3067-3073.
Pomerantseva et al., Degradation behavior of poly(glycerol sebacate), Journal of Biomedical Materials Research Part A, 91A: 1038-1047 (2008).
Robinson et al., Extracellular Matrix Scaffold and Cardiac Repair, Circulation, 112(43): 135-143 (2005).
Ruvinov et al. The promotion of myocardial repair by the sequential delivery of IGF-1 and HGF from an injectable alginate biomaterial in a model of acute myocardial infarction, Biomaterials, 32: 565-578 (2011).
Serrano et al., Advances and Applications of Biodegradable Elastomers in Regenerative Medicine, Advanced Functional Materials, 20: 192-208 (2010).
Stuckey et al., Magnetic Resonance Imaging Evaluation of Remodeling by Cardiac Elastomeric Tissue Scaffold Biomaterials in a Rat Model of Myocardial Infarction, Tissue Engineering Part A, 16:3395-3402 (2010).
Theron et al., Modification, crosslinking and reactive electrospinning of a thermoplastic medial polyurethane for vascular graft applications, Acta Biomaterialia, 6: 2434-2447 (2010).
Wang et al., A tough biodegradable elastomer, Nature Biotechnology, 20: 602-606 (2002).
Yang et al., Novel itric Acid-baed Biodegradanle Elastomers for Tissue Engineering, Advanced Materials, 16(6): 511-516 (2004).
Zdrahala et al., Biomedical Applications of Polyurethanes: A Review of Past Promises, Present Realities and a Vibrant Future, Journal of Biomaterials Applications, 14(1): 67-90 (1999).

* cited by examiner

URETHANE-CROSSLINKED BIODEGRADABLE ELASTOMERS

RELATED REFERENCES

This application claims priority to U.S. provisional patent application Ser. No. 61/527,879, filed Aug. 26, 2011, the entire contents of which are herein incorporated by reference.

GOVERNMENT SUPPORT

This invention was made with government support under Grant Nos. DE013023 and GM086433 awarded by the National Institutes of Health, and under Grant No. BES0609182 awarded by the National Science Foundation. The government has certain rights in this invention.

BACKGROUND

Biodegradable elastomers have emerged as promising materials for their potential to mimic the viscoelastic properties of several tissues and exhibit compliance with dynamic environments without damaging the surrounding tissue. However, there remains a continuing need for new such biodegradable elastomer materials. In particular, the development of highly tunable biodegradable elastomers that can effectively and controllably present biological and physical signals and withstand repeated cycles of physiologic loads, has remained elusive.

SUMMARY

In various aspects, the present disclosure provides elastomeric materials (e.g., biodegradable elastomers), compositions containing them (e.g., precursor compositions), and methods for their production and use. In particular, the present invention provides compositions comprising a polyester material together with and/or crosslinked by a polyisocyanate crosslinker. The present invention therefore provides elastomeric materials that include at least one urethane crosslink covalently linking polymer components within the material to one another.

In some embodiments, an elastomeric cross-linked polyester material comprises a plurality of polymeric units of the general formula $(-A-B-)_p$, wherein p is an integer greater than 1; and a plurality of urethane cross-links each of which covalently links two polymeric units to one another, which two linked polymeric unit each had at least one free hydroxyl or amino group prior to formation of the crosslink, wherein each (-A-B—) polymeric unit has a chemical structure that is achieved when a polyol component A' is condensed with a polyacid component B', so that each -A- component represents a substituted or unsubstituted ester and each —B— component represent a substituted or unsibstituted ester comprising at least two acid ester functionalities.

In some embodiments, a method of making an elastomeric cross-linked polyester material comprising 1) providing a polyester material comprising a polymeric unit of the general formula $(-A-B-)_p$, wherein: A-B has a chemical structure that is achieved when a polyol component A' is condensed with a polyacid component B'; and at least two A-B units in the material each have at least one free hydroxyl or amino group, and 2) mixing the polyester material with a polyisocyanate so that an elastomeric crosslinked polyester material is produced.

DEFINITIONS

Figure 1:
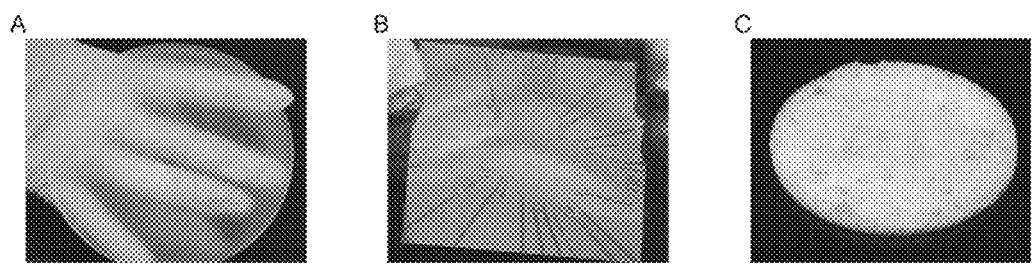
FIG. 1 shows macroscopic appearance of A) representative PGSU-S films, B) representative non-porous PGSU-SF films prepared through spin coat method, and C) representative porous PGSU-SF films.

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Associated": As used herein, the term "associated" typically refers to two or more moieties connected with one another, either directly or indirectly (e.g., via one or more additional moieties that serve as a linking agent), to form a structure that is sufficiently stable so that the moieties remain connected under conditions in which the structure is used, e.g., physiological conditions. In some embodiments, associated moieties are attached to one another by one or more covalent bonds. In some embodiments, associated moieties are attached to one another by a mechanism that involves specific (but non-covalent) binding (e.g. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Hydrolytically degradable": As used herein, "hydrolytically degradable" materials are those that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Nucleic acid": The term "nucleic acid" as used herein, refers to a polymer of nucleotides. In some embodiments, nucleic acids are or contain deoxyribonucleic acids (DNA); in some embodiments, nucleic acids are or contain ribonucleic acids (RNA). In some embodiments, nucleic acids include naturally-occurring nucleotides (e.g., adenosine, thymidine, guanosine, cytidine, uridine, deoxyadenosine, deoxythymidine, deoxyguanosine, and deoxycytidine). Alternatively or additionally, in some embodiments, nucleic acids include non-naturally-occurring nucleotides including, but not limited to, nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups. In some embodiments, nucleic acids include phosphodiester backbone linkages; alternatively or additionally, in some embodiments, nucleic acids include one or more non-phosphodiester backbone linkages such as, for example, phosphorothioates and 5'-N-phosphoramidite linkages. In some embodiments, a nucleic acid is an oligonucleotide in that it is relatively short (e.g., less that about 5000, 4000, 3000, 2000, 1000, 900, 800, 700, 600, 500, 450, 400, 350, 300, 250, 200, 150, 100, 90, 80, 70, 60, 50, 45, 40, 35, 30, 25, 20, 15, 10 or fewer nucleotides in length).

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polypeptide": The term "polypeptide" as used herein, refers to a string of at least three amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, http://www.cco.caltech.edu/dadgrp/Unnatstruct.gif, which displays structures of non-natural amino acids that have been successfully incorporated into functional ion channels) and/or amino acid analogs as are known in the art may alternatively be employed). In some embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g, modified sugars such as 2'-fluororibose, 2'-deoxyribose, and hexose).

"Small molecule": As used herein, the term "small molecule" is used to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present application.

"Substantial" or "substantive": As used herein, the terms "substantial" or "substantive" and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Transparent": As used herein, the term "transparent" refers to a sample specimen with a light transmission percentage of at least 75%, at least 80%, at least 85%, at least 90%, at least 95%, or at least 99%. It is possible to measure the degree of light transmission using ASTM D-1003 (Standard Test Method for Haze and Luminous Transmittance of Transparent Plastics), and this test method is used to evaluate light transmission and scattering of transparent plastics for a defined specimen thickness. In some embodiments, the term may refer to a sample specimen which has a constant refractive index through the sample in the viewing direction. The perceived transparency or optical clarity is dependent on the thickness of the sample used for assessment, and the optical clarity will decrease with increasing thickness. Any areas of opaque material (such as colorants) or areas of different refractive index, will result in a loss of optical clarity due to refraction and scattering. Optical clarity is also dependent on surface reflections from the sample.

"Treating": As used herein, the term refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

It will be appreciated that pre-polymer and polymer components such as polyol and polycarboxylic acid, used to make inventive elastomeric compositions and materials, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds.

In certain aspects, the term "substituted" is also contemplated to include substitution with a "biologically-active agent," or substitution with another inventive elastomeric material, as defined herein.

The term "aliphatic," as used herein, includes both saturated and unsaturated, nonaromatic, straight chain (i.e., unbranched), branched, acyclic, cyclic (i.e., carbocyclic), or polycyclic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (for example, an aliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, phosphino, cyano, amino, azido, nitro, hydroxy, thio, and/or halo groups).

The term "heteroaliphatic," as used herein, refers to an aliphatic moiety, as defined herein, that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. Heteroaliphatic group substituents include, but are not limited to, any of the substituents described herein, that result in the formation of a stable moiety (for example, a heteroaliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-12 carbon atoms. In still other embodiments, the alkyl group contains 1-6 carbon atoms. In yet another embodiments, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety (for example, an alkyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-10 carbon atoms. In another embodiment, the alkenyl group employed contains 2-8 carbon atoms. In still other embodiments, the alkenyl group contains 2-6 carbon atoms. In yet another embodiments, the alkenyl group contains 2-4 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (for example, an alkenyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-10 carbon atoms. In another embodiment, the alkynyl group employed contains 2-8 carbon atoms. In still other embodiments, the alkynyl group contains 2-6 carbon atoms. In still other embodiments, the alkynyl group contains 2-4 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (for example, an alkynyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkylene," as used herein, refers to a fully saturated straight- or branched-chain alkyl biradical containing between one and twenty carbon atoms by removal of two hydrogen atoms (the term alkyl is defined herein). In certain embodiments, an alkylene group is substituted by independent replacement of one or more of the hydrogen atoms thereon with one or more substituents. Alkylene group substituents include but are not limited to any of the substituents described herein that result in the formation of a stable moiety (such as, for example, an alkylene group substituted with one or more aliphatic, heteroaliphatic, heterocyclic, aryl, heteroaryl, acyl, sulfinyl, sulfonyl, cyano, amino, azido, nitro, hydroxyl, thiol, and/or halo groups).

The term "alkenylene," as used herein, refers to a straight- or branched-chain alkenyl biradical containing between two and twenty carbon atoms by removal of two hydrogen atoms (the term alkenyl is defined herein). In certain embodiments, an alkenylene group is substituted by independent replacement of one or more of the hydrogen atoms thereon with one or more substituents. Alkenylene group substituents include but are not limited to any of the substituents described herein that result in the formation of a stable moiety (such as, for example, an alkenylene group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxyl, thiol, and/or halo groups).

The term "alkynylene" as used herein, refers to a straight- or branched-chain alkynyl biradical containing between two and twenty carbon atoms by removal of two hydrogen atoms (the term alkynyl is defined herein). In certain embodiments, an alkynylene group is substituted by independent replacement of one or more of the hydrogen atoms thereon with one or more substituents. Alkynylene group substituents include but are not limited to any of the substituents described herein that result in the formation of a stable moiety (such as, for example, an alkynylene group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxyl, thiol, and/or halo groups).

The term "heteroalkylene," as used herein, refers to an alkylene group, as defined herein, that contains one or more oxygen, sulfur, nitrogen, phosphorus, or silicon atoms, e.g., in place of carbon atoms.

The term "heteroalkenylene," as used herein, refers to an alkenylene group, as defined herein, that contains one or more oxygen, sulfur, nitrogen, phosphorus, or silicon atoms, e.g., in place of carbon atoms.

The term "heteroalkynylene," as used herein, refers to an alkynylene group, as defined herein, that contains one or more oxygen, sulfur, nitrogen, phosphorus, or silicon atoms, e.g., in place of carbon atoms.

The term "heterocyclic," or "heterocyclyl," as used herein, refers to an non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (for example, a heterocyclic group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (for example, an aryl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (for example, a heteroaryl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "acyl," as used herein, refers to a group having the general formula $—C(=O)R$, where R is hydrogen, halogen, hydroxyl, thiol, optionally substituted amino, optionally substituted hydrazino, optionally substituted aliphatic, optionally substituted heteroaliphatic, optionally substituted alkyl, optionally substituted alkenyl, optionally substituted alkynyl, optionally substituted aryl, alkyloxy, alkylthioxy, alkylamino, dialkylamino, arylamino, diarylamino, optionally substituted aryl, optionally substituted heteroaryl, or optionally substituted heterocycyl. Exemplary acyl groups include aldehydes (—CHO), carboxylic acids (—$CO_2$H), ketones (such as an acetyl group [—(C=O)$CH_3$], esters, amides, carbonates, carbamates, and ureas. Acyl substituents include, but are not limited to, any of the substituents described herein, that result in the formation of a stable moiety (for example, a heteroaryl group substituted with one or more aliphatic, alkyl, alkenyl, alkynyl, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "hydroxy," or "hydroxyl," as used herein, refers to a group of the formula (—OH). An "optionally substituted hydroxy" refers to a group of the formula (—$OR^i$), wherein $R^i$ can be hydrogen, or any substitutent which results in a stable moiety (for example, a hydroxy group substituted with a suitable hydroxyl protecting group, an aliphatic, alkyl, alkenyl, alkynyl, heteroaliphatic, heterocyclic, aryl, heteroaryl, acyl, sulfinyl, and/or sulfonyl group).

The term "amino," as used herein, refers to a group of the formula (—$NH_2$). An "optionally substituted amino" refers to a group of the formula (—$NR^h{}_2$), wherein $R^h$ can be hydrogen, or any substitutent. Substituents include, but are not limited to, any of the substituents described herein, that result in the formation of a stable moiety (for example, an amino group substituted with one or more aliphatic, alkyl, alkenyl, alkynyl, heteroaliphatic, heterocyclic, aryl, heteroaryl, acyl, sulfinyl, sulfonyl, amino, nitro, hydroxy, and/or thio groups).

DETAILED DESCRIPTION OF CERTAIN EMBODIMENTS

The present disclosure provides, among other things, elastomeric materials, compositions, and methods of use and preparation. Provided materials are useful in a variety of medical and non-medical applications. For example, provided materials have many different useful applications, including in drug delivery (e.g., for the delivery of therapeutic, diagnostic, or other agents) and in tissue engineering, (e.g., of tissue reconstruction, and medical patches).

In various embodiments, elastomeric cross-linked polyester materials are formed by the reaction of a multifunctional polyether or polyol component. A' (i.e., a component comprising two or more OR groups, where each R is independently H and an alkyl) with a polyacid component B' (that is a component having a difunctional or higher order acid) to form a pre-polymer $(-A-B—)_p$, wherein p is an integer greater than 1. Cross-linking of the pre-polymer generates elastomeric polyester materials. In some embodiments, cross-linking is performed by functionalization of hydroxyl group or amino groups on a pre-polymer backbone or side chain with a polyisocyanates, to form an elastomeric cross-linked polyester material that contains one or more urethane crosslinks.

In some embodiments, an elastomeric cross-linked polyester material comprises a plurality of polymeric units of the general formula $(-A-B—)_p$, wherein p is an integer greater than 1; and a plurality of urethane cross-links each of which covalently links two A components to one another, which two linked A components each had at least one free hydroxyl group or amino groups prior to formation of the crosslink.

In some embodiments, a pre-polymer is a polyester material comprising a polymeric unit of the general formula (-A-B—)$_p$ wherein p is an integer greater than 1, and further wherein: A-B has a chemical structure that is achieved when a polyol component A' is condensed with a polyacid component B'; and at least two A-B units in the material each has at least one free hydroxyl group or amine group.

In some embodiments, a pre-polymer is a polyester further comprising a polyamide backbone. For example, polyamine (that is a component comprising two or more amino groups) can be used to react with polyacid together with polyol or after reacting with polyol. Exemplary poly (ester amide) includes those described in Cheng, et al., *Adv. Mater.* 2011, 23, 1195-11100, the contents of which are herein incorporated by reference. Without being hound to any particular theory, amides can form hydrogen bonds, which may affect the elasticity and/or mechanical properties of materials.

Pre-Polymer

A pre-polymer used in accordance with the present disclosure may be linear or branched (i.e., non-linear). A pre-polymer, in some embodiments, is biodegradable and/or biocompatible.

In some embodiments, a pre-polymer is a polyester material comprising a polymeric unit of the general formula (-A-B—)$_p$, wherein p is an integer greater than 1. In some embodiments, A represents a substituted or unsubstituted ester, wherein A comprises at least a hydroxyl group or amine group prior to crosslinking, while B represents a substituted or unsubstituted ester comprising at least two acid ester functionalities.

In some embodiments, a pre-polymer is a polyester material comprising two or more different As or Bs. In some embodiments, each A independently represents a substituted or unsubstituted ester, wherein each A comprises at least a hydroxyl group or amine group prior to crosslinking at least one free hydroxyl group or amino group; and/or each B independently has represents a substituted or unsubstituted ester comprising at least two acid ester functionalities. For example, such a pre-polymer can be formed by reacting one or more different polyol components A' (e.g., a first polyol with a free hydroxyl group and a second polyol with a free amino group, at various ratios) with one or more polyacid components B'.

In some embodiments, polyol-based polymers described in US Patent Application Publication No. 2011-0008277, U.S. Pat. No. 7,722,894 and U.S. Pat. No. 8,143,042, the contents of which are hereby incorporated by reference, are used as a pre-polymer to form an elastomeric cross-linked polyester material.

In certain embodiments, a pre-polymer can have the following formula:

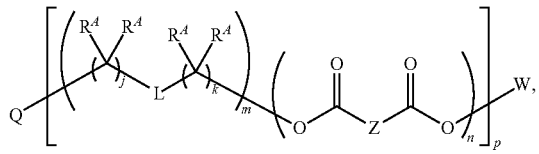

wherein:

each instance of Z and L, are, independently, cyclic or acylic, branched or unbranched, substituted or unsubstituted alkylene; cyclic or acylic, branched or unbranched, substituted or unsubstituted alkenylene; cyclic or acylic, branched or unbranched, substituted or unsubstituted alkynylene; cyclic or acylic, branched or unbranched, substituted or unsubstituted heteroalkylene; cyclic or acylic, branched or unbranched, substituted or unsubstituted heteroalkenylene; cyclic or acylic, branched or unbranched, substituted or unsubstituted heteroalkynylene; substituted or unsubstituted arylene; substituted or unsubstituted heteroarylene; or substituted or unsubstituted acylene;

each instance of $R^A$ is, independently, hydrogen; Q; $OR^C$; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl; or two $R^A$ groups are joined to form (=O), (=S), or (=$NR^B$), wherein $R^B$ is hydrogen; a suitable amino protecting group; substituted or unsubstituted amino; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl;

W is hydrogen, or a suitable carboxylic acid protecting group;

Q is —$OR^C$, wherein $R^C$ is hydrogen, acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl;

and $R^A$ and/or L comprises at least a free hydroxyl/amino group prior to crosslinking.

In certain embodiments, $R^A$ is hydrogen.

In certain embodiments, L is hydroxyl-substituted methylene (i.e., —CH(OH)—).

In certain embodiments, j is 0 to 6. In certain embodiments, k is 0 to 6.

In certain embodiments, m is 1 to 100. In certain embodiments, m is 1 to 50. In certain embodiments, m is 1 to 25. In certain embodiments, m is 1 to 10. In certain embodiments, m is 1 to 5. In certain embodiments, m is 1 to 4. In certain embodiments, m is 1 to 3. In certain embodiments, m is 1 to 2. In certain embodiments, m is 1.

In certain embodiments, n is 1 to 100. In certain embodiments, n is 1 to 50. In certain embodiments, n is 1 to 25. In certain embodiments, n is 1 to 10. In certain embodiments, n is 1 to 5. In certain embodiments, n is 1 to 4. In certain embodiments, n is 1 to 3. In certain embodiments, n is 1 to 2. In certain embodiments, n is 1.

In certain embodiments, p is 1 to 900. In certain embodiments, p is 1 to 800. In certain embodiments, p is 1 to 700.

In certain embodiments, p is 1 to 600. In certain embodiments, p is 1 to 500. In certain embodiments, p is 1 to 400. In certain embodiments, p is 1 to 300. In certain embodiments, p is 1 to 200. In certain embodiments, p is 1 to 100. In certain embodiments, p is 1 to 50. In certain embodiments, p is 1 to 25. In certain embodiments, p is 1 to 10. In certain embodiments, p is 1 to 5. In accordance with the present disclosure, p varies depending on the repeat unit of A and B, in some embodiments, to achieve a suitable molecular weight of a pre-polymer.

In some embodiments, a pre-polymer has a molecular weight greater than about 3000 Da, about 4000 Da, about 5000 Da, about 6000 Da, about 7000 Da, about 8000 Da, about 9000 Da, about 10000 Da, about 11000 Da, about 12000 Da, about 13000 Da, about 14000 Da, about 15000 Da, about 16000 Da, about 17000 Da, about 18000 Da, about 19000 Da, about 20000 Da, about 25000 Da, or about 50000 Da. In some embodiments, a pre-polymer has a molecular weight less than about 4000 Da, about 5000 Da, about 6000 Da, about 7000 Da, about 8000 Da, about 9000 Da, about 10000 Da, about 11000 Da, about 12000 Da, about 13000 Da, about 14000 Da, about 15000 Da, about 16000 Da, about 17000 Da, about 18000 Da, about 19000 Da, about 20000 Da, about 25000 Da, about 50000 Da, or about 100000 Da. In some embodiments, a pre-polymer has a molecular weight ranging from about 3000 Da to 50000 Da, from about 5000 Da to 30000 Da, or of any two values above.

In some embodiments, a pre-polymer for use in accordance with the present invention has a molecular weight within a range between a lower boundary and an upper boundary. In some embodiments, the lower boundary is selected from the group consisting of about 3000 Da, about 4000 Da, about 5000 Da, about 6000 Da, about 7000 Da, about 8000 Da, about 9000 Da, about 10000 Da, about 11000 Da, about 12000 Da, about 13000 Da, about 14000 Da, about 15000 Da, about 16000 Da, about 17000 Da, about 18000 Da, about 19000 Da, about 20000 Da, about 25000 Da, and about 50000 Da; in some embodiments, the upper boundary is selected from the group consisting of about 4000 Da, about 5000 Da, about 6000 Da, about 7000 Da, about 8000 Da, about 9000 Da, about 10000 Da, about 11000 Da, about 12000 Da, about 13000 Da, about 14000 Da, about 15000 Da, about 16000 Da, about 17000 Da, about 18000 Da, about 19000 Da, about 20000 Da, about 25000 Da, about 50000 Da, and about 100000 Da. Without being bound to any particular theory, a molecular weight of a pre-polymer can affect the crosslinking rate and density.

As illustrated in the Examples provided herein, the present invention demonstrates, among other things, that certain elastomeric materials as described herein with surprisingly good and/or useful properties are generated through use of a pre-polymer whose molecular weight is within the range of 5000 Da to 20000 Da or 9000 Da to 15000 Da.

In some embodiments, a pre-polymer described herein can be formed when a polyol component A' is condensed with a polyacid component B'; and at least two A-B units that is achieved each has at least one free hydroxyl or amino group.

In some embodiments, a wide variety of a polyol component A', can be used in the production of elastomeric compositions and materials according to various embodiments of the present disclosure. In certain embodiments, a polyol component A' is selected from Table 1 (provided below). In certain embodiments, a polyol component A' is selected from glycerol, erythritol, threitol, ribitol, arabinitol, xylitol, allitol, altritol, galactitol, sorbitol, mannitol, iditol, lactitol, isomalt, or maltitol, wherein the functional groups present on the polyol are optionally substituted, as described above. In certain embodiments, a polyol component A' is selected from xylitol, mannitol, sorbitol, or maltitol, wherein the functional groups present on the polyol are optionally substituted, as described above.

TABLE 1

Exemplary polyols

Sugar alchols glycerol; glyceritol; Propane-1,2,3-triol erythritol threitol ribitol; adonitol arabinitol xylitol

TABLE 1-continued

Exemplary polyols allitol, altritol, galactitol glucitol; sorbitol, mannitol, iditol Cyclic sugars
Maltitol, lactitol, isomalt e.g., maltitol e.g., lactitol e.g., isomalt e.g., monosaccharides which include hexoses (allose, altrose, glucose, mannose, gulose, idose, galactose, talose) and pentoses (ribose, arabinaose, xylose, lyxose); disaccharides which include maltose, cellobiose, sucrose, and lactose; polysaccharides which include amylose, amylopectin, glycogen, and cellulose; fructofuranose, glucopyranose, sorbose, rhaminose, tagatose, apiose, deoxyribose,ribofructose, 1,3,6-tri-O-galloyl-β-D-glucopyranose (tannic acid); amino-containing cyclic sugars (e.g., N-acetyl glucoseamine (sialic acid), glucoseamine); amide-containing cyclic sugars (e.g., glucoronamide); carboxyl containing sugars (e.g., galacturonic acid); as well as protected derivatives, such as alkyl- and acyl- derivatives, and stereoisomers thereof.

TABLE 1-continued

Exemplary polyols

| | |
|---|---|
| Pentaerythritols, and structural derivatives thereof, such as methylated, ethylated, acetate, ethoxylate, and propoxylate derivatives. | e.g., 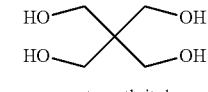 pentaerythritol 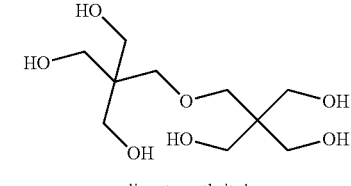 dipentaerythritol 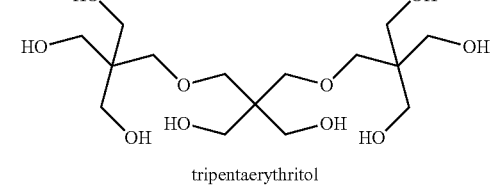 tripentaerythritol |
| Phenolic polyols | e.g., resorcinol, orcinol, 2-methylresorcinol, phloroglucinol, 1,2,4 benzenetriol, pyrogallol, 4-ethylresorcinol, 5-methyl benzene1,2,3triol, 2-methoxyhydroquinone, 3,5dihydroxylbenzyl alcohol, 2,4,6 trihydroxytoluene, 2,4,5-trihydroxybenzaldehyde, 2,3,4-trihydroxybenzaldehyde, 2,4,6,-trihydroxybenzaldehyde, gallacetophenone, 3,4,5-trihydroxybenzamide, gallic acid, 2,4,5-trihydroxybenzoic acid, 2,3,4-trihydroxybenzoic acid, 2-nitrophloroglucinol; naturally occurring phenolic compounds, such as carnosol, rosmanol (7α-), epirosmanol (7β-) from rosemary (Rosmarinus officialis L.); rosemaric acid from rosemary and oregano (Oreganum vulgare L.); capsicin and dihydrocapsicin, hot-tasting compounds, from hot pepper (Capsicinum annuum L.); ferulic acid amide of tyramine from black pepper (Piper nigrum L.); piperin-related compound from thyme (Thymus serpyllum L.); and apigenin and apiin from parsley |
| Miscellaneous polyols | e.g., 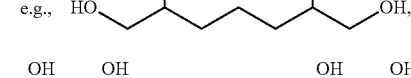 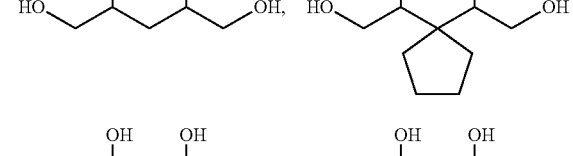 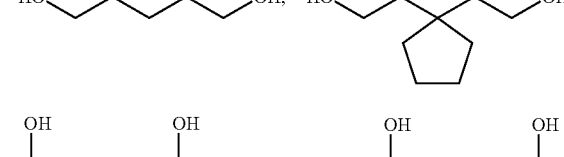 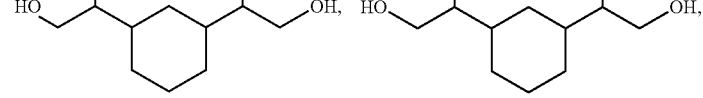 |

TABLE 1-continued

Exemplary polyols

[Chemical structures of exemplary polyols]

In some embodiments, any of a wide variety of a polyacid component B', can be used in the production of elastomeric compositions and materials according to various embodiments of the present disclosure, including, but are not limited to, glutaric acid (5 carbons), adipic acid (6 carbons), pimelic acid (7 carbons), suberic acid (8 carbons), and azelaic acid (nine carbons). Exemplary long chain diacids include diacids having more than 10, more than 15, more than 20, and more than 25 carbon atoms. Non-aliphatic diacids can be used. For example, versions of the above diacids having one or more double bonds can be employed to produce glycerol-diacid co-polymers. Amines and aromatic groups can be incorporated into the carbon chain. Exemplary aromatic diacids include terephthalic acid and carboxyphenoxypropane. The diacids can also include substituents as well. For example, in various embodiments, reactive groups like amino and hydroxyl can be used increase the number of sites available for cross-linking. In various embodiments, amino acids and other biomolecules can be used to modify the biological properties of elastomeric materials. In various embodiments, aromatic groups, aliphatic groups, and halogen atoms can be used to modify the inter-chain interactions within elastomeric materials.

In certain embodiments, a polyacid component B' is selected from Table 2 (provided below). In certain embodiments, a polyacid component B' is selected from the group consisting of succinic acid, fumaric acid, α-ketoglutaric acid, oxaloacetic acid, malic acid, oxalosuccinic acid, iso-citric acid, cis-aconitic acid, citric acid, 2-hydroxy-malonic acid, tartaric acid, ribaric acid, arabanaric acid, xylaric acid, allaric acid, altraric acid, galacteric acid, glucaric acid, or mannaric acid, dimercaptosuccinic acid, oxalic acid, malonic acid, succinic acid, glutaric acid, adipic acid, pimelic acid, suberic acid, azelaic acid, and sebacic acid, wherein the functional groups present on polycarboxylic acids are optionally substituted, as described above. In certain embodiments, a polyacid component B' is citric acid. In certain embodiments, a polyacid component B' is sebacic acid. In certain embodiments a polyacid component B' is a polycarboxylic acid selected from glutaric acid, citric acid and sebacic acid, wherein the functional groups present on polycarboxylic acids are optionally substituted, as described herein.

TABLE 2

Exemplary Polycarboxylic Acids

| | |
|---|---|
| Oxalic acid | [structure] |
| Malonic acid (propanedioic acid) | [structure] |
| Succinic acid, succinate (butanedioic acid) | [structure] |
| Glutaric acid (pentanedioic acid) | [structure] |
| Adipic acid (hexanedioic acid) | [structure] |

TABLE 2-continued

Exemplary Polycarboxylic Acids

Pimelic acid
(heptanedioic acid)

HOOC-(CH2)5-COOH

Suberic acid
(octanedioic acid)

HOOC-(CH2)6-COOH

Azelaic acid
(nonanedioic acid)

HOOC-(CH2)7-COOH

Sebacic acid
(decanedioic acid)

HOOC-(CH2)8-COOH

Aldaric acids

2-Hydroxy-malonic acid tartaric acid (erythrose)

tartaric acid (threose)

ribaric acid arabanaric acid xylaric acid allaric acid altraric acid galacteric acid gulcaric acid mannaric acid TABLE 2-continued Exemplary Polycarboxylic Acids Aspartic acid L-aspartic acid DMSA
(Dimercapto-succinic acid,
2,3-bis-sulfanylbutanedioic
acid)

fumaric acid maleic acid glutaconic acid glutamic
Acid, Gln, Glutamate

α-ketoglutaric acid;
Oxopentanedioic acid;

β-ketoglutaric acid

Oxaloacetic acid;
Oxaloacetate;

Malic acid;
Malate; hydroxysuccinic acid e.g., L-Malic acid fumaric acid;
fumarate TABLE 2-continued Exemplary Polycarboxylic Acids

| Name | Structure |
|---|---|
| oxalosuccinic acid; oxalosuccinate | |
| isocitric acid; isocitrate | |
| cis-aconitic acid | |
| Citric acid; citrate | |
| Itaconic acid; methylenesuccinic acid | |
| mesaconic acid; (2E)-2-Methyl-2-butenedioic acid | |
| Tartaric acid, 2,3-dihydroxybutanedioic acid, ,3-dihydroxysuccinic acid; threaric acid; uvic acid; paratartaric acid | |
| Traumatic acid; dodec-2-enedioic acid | |

Urethane Crosslinking

Cross-linking can be performed by functionalization of hydroxyl group or amino groups on a pre-polymer backbone or side chain with a polyisocyanate (that is a component having a difunctional or higher order isocyanate), to form an elastomeric cross-linked polyester material that contains one or more urethane crosslinks. In some embodiments, in addition to chemical interchain crosslinks (e.g., urethane linkages), physical interchain crosslinks are formed in an elastomeric cross-linked polyester material. Exemplary physical crosslinks are based on hydrogen bonding interactions, affinity interactions, metal coordination, physical adsorption, host-guest interactions, hydrophobic interactions, pi stacking interactions, van der Waals interactions, magnetic interactions, electrostatic interactions, and dipole-dipole interactions.

Various polyisocyanates can be used for crosslinking in accordance with the present disclosure. In some embodiments, polyisocyanates for use in the present invention include aliphatic polyisocyanates. Exemplary aliphatic polyisocyanates include, but are not limited to, lysine diisocyanate, an alkyl ester of lysine diisocyanate (for example, the methyl ester or the ethyl ester), lysine triisocyanate, hexamethylene diisocyanate, isophorone diisocyanate (IPDI), 4,4'-dicyclohexylmethane diisocyanate ($H_{12}$MDI), cyclohexyl diisocyanate, 2,2,4-(2,2,4)-trimethylhexamethylene diisocyanate (TMDI), dimers prepared form aliphatic polyisocyanates, trimers prepared from aliphatic polyisocyanates and/or mixtures thereof. In some embodiments, hexamethylene diisocyanate (HDI) trimer sold as Desmodur N3300A can be a polyisocyanate utilized in the present invention.

Methods

The present inventions among other things provide methods of forming biodegradable elastomeric compositions and materials. In some embodiments, elastomeric compositions and materials are used to form structures (e.g., scaffold) and/or to coat devices.

To make a pre-polymer, various molar ratios of polyol to polyacid can be used in accordance with the present disclosure. In some embodiments, such a molar ratio is more or less than about 1:0.1, about 1:0.2, about 1:0.3, about 1:0.4, about 1:0.5, about 1:0.6, about 1:0.7, about 1:0.8, about 1:0.9, about 1:1, about 1:1.1, about 1:1.2, about 1:1.3, about 1:1.4, about 1:1.5, about 1:1.6, about 1:1.7 about 1:1.8 about 1:1.9, about 1:2 or about 1:2.5. In some embodiments, such a ratio is in a range of 1:0.5 to 1:2, or between any two values above.

As appreciated by a person of ordinary skill in the art, a molar ratio of a free reactive group (e.g., a hydroxyl or amino group) of a pre-polymer to a polyisocyanate or a reactive isocyanate group of a polyisocyanate dictates the crosslinking rate and density. Such a molar ratio can vary to adjust properties of an elastomeric cross-linked polyester material formed after crosslinking. In some embodiments, such a ratio is more or less than about 1:0.1, about 1:0.2, about 1:0.3, about 1:0.4, about 1:0.5, about 1:0.6, about 1:0.7, about 1:0.8, about 1:0.9, about 1:1, about 1:1.1, about 1:1.2, about 1:1.3, about 1:1.4, about 1:1.5, about 1:1.6, about 1:1.7 about 1:1.8 about 1:1.9, about 1:2 or about 1:2.5. In some embodiments, such a molar ratio is in a range of 1:0.3 to 1:1, 1:0.5 to 1:0.8 or between any two values above.

As illustrated in the Examples provided herein, the present invention demonstrates, among other things, that certain elastomeric materials as described herein can be prepared at low temperature rapidly by crosslinking a pre-polymer with polyisocyanate. The temperature at which the production of a pre-polymer is performed can be higher than that for crosslinking. In some embodiments, crosslinking a pre-polymer with polyisocyanate in accordance with the present disclosure is conducted at a temperature less than about 100° C., about 90° C., about 80° C., about 70° C., about 60° C., about 55° C., about 50° C., about 45° C., about 40° C., about 35° C., about 30° C., about 35° C., about 30° C., about 25° C., or even about 20° C.

In some embodiments, production of a pre-polymer and crosslinking are done in one step. Alternatively, production of a pre-polymer is followed by crosslinking in a two-step process.

In some embodiments, production of a pre-polymer is followed by crosslinking in the presence of at least one solvent. In some embodiments, production of a pre-polymer is followed by crosslinking surprisingly in a solvent free condition. In certain embodiments, a solvent-free crosslinking is conducted at a room temperature. In certain embodiments, a solvent-free crosslinking is conducted at a body temperature, which is particularly useful for in situ crosslinking of a pre-polymer.

In some embodiments, at least one catalyst is used for crosslinking with polyisocyanate. A catalyst, for example, can be non-toxic (in a concentration that may remain in elastomeric compositions and materials).

In some embodiments, a catalyst is an organometallic compound. In some embodiments, catalyst is a tertiary amine compound. Exemplary catalysts includes, but are not limited to, stannous octoate (an organobismuth compound), triethylene diamine, bis(dimethylaminoethyl)ether, dimethylethanolamine, dibutyltin dilaurate, and Coscat organometallic catalysts manufactured by Vertullus (a bismuth based catalyst), or any combination thereof.

A porogen may be used to generate porous elastomeric compositions and materials. In some embodiments, a porogen reserves space in an elastomeric composition or material in the process of formation and then the porogen diffuses, dissolves, or degrades, thereby inducing porosity into the formed elastomeric composition or material. In this way porogens provide latent pores. In some embodiments, a porogen is leached out of an elastomeric composition or material before use.

A porogen may be a gas (e.g., carbon dioxide, nitrogen, or other inert gas), liquid (e.g., water, biological fluid), or solid. In some embodiments, porogens are water soluble such as salts, sugars (e.g., sugar alcohols), polysaccharides (e.g., dextran (poly(dextrose)), water soluble small molecules, etc. Additionally or alternatively, porogens can be natural or synthetic polymers, oligomers, or monomers that are water soluble or degrade quickly under physiological conditions. Exemplary polymeric porogens include polyethylene glycol, poly(vinylpyrollidone), pullulan, poly(glycolide), poly(lactide), poly(lactide-co-glycolide), other polyesters, and starches.

Material Properties

In various embodiments, an elastomeric cross-linked polyester material formed from the a composition of the present invention, has one or more of characteristics including Young's modulus, tensile strength, elongation, size deformation, transparency to light, etc.

In some embodiments, an elastomeric material has Young's modulus more or less than about 0.2 MPa, about 0.5 MPa, about 1 MPa, about 2 MPa, about 5 MPa, about 8 MPa, about 10 MPa, about 12 MPa, about 15 MPa, about 18 MPa, about 20 MPa, about 22 MPa, about 25 MPa, about 28 MPa, about 30 MPa, about 40 MPa or even 50 MPa. In some embodiments, an elastomeric material has Young's modulus in a range of 0.5 MPa and 25 MPa, 1 MPa and 20 MPa, 5 MPa and 15 MPa, or any two values above.

In some embodiments, an elastomeric material has a tensile strength more or less than about 0.2 MPa, about 0.5 MPa, about 1 MPa, about 2 MPa, about 5 MPa, about 8 MPa, about 10 MPa, about 12 MPa, about 15 MPa, about 18 MPa, about 20 MPa, about 22 MPa, about 25 MPa, about 28 MPa, about 30 MPa, about 40 MPa or even 50 MPa. In some embodiments, an elastomeric material has a tensile strength in a range of about 0.5 MPa and about 15 MPa, about 1 MPa and about 10 MPa, or any two values above.

In some embodiments, an elastomeric material has an elongation more or less than about 10%, about 20%, about 50%, about 80%, about 100%, about 150%, about 200%, about 300%, about 400%, about 500%, about 600%, about 700%, or about 800%. In some embodiments, an elastomeric material has an elongation in a range of about 50% and about 600%, about 200% and about 500%, or any two values above.

In some embodiments, an elastomeric material has size deformation below than about 5%, about 10%, about 15%, about 20%, about 30%, about 40%, or even about 50% of its initial length, after tensile loading.

In some embodiments, an elastomeric material has a tensile strength stable within about 1%, about 2%, about 3%, about 5%, about 10%, about 15%, about 20%, about 25%, about 30%, about 35%, about 40%, about 45%, or about 50% of the initial sample strength over 100 cycles of extension.

In some embodiments, an elastomeric material has size deformation stable within about 1%, about 2%, about 3%, about 5%, about 10%, about 15%, about 20%, about 25%, about 30%, about 35%, about 40%, about 45%, or about 50% of the initial sample length over 100 cycles of extension.

In some embodiments, an elastomeric material is substantially transparent to light before and/or after exposure to water. For example, the transparency can be tested when an elastomeric material is made into a non-porous film form with a thickness of 200 μm. In certain embodiments, an elastomeric material in a non-porous film form with a thickness of 200 um has a light transmission percentage more than about 75%, about 80%, about 85%, about 90%, about 95%, or about 99%.

As illustrated in the Examples provided herein, the present invention demonstrates, among other things, that certain elastomeric materials as described herein with surprisingly transparency to light after exposure to water.

Agents for Delivery

Elastomeric compositions and materials in accordance with the present invention can comprise one or more agents for delivery. In some embodiments, one or more agents are associated independently with an elastomeric material.

In some embodiments, an agent for delivery associated with an elastomeric material is released when the elastomeric material degrades. Additionally or alternatively, an agent is release by diffusion.

In theory, any agents including, for example, therapeutic agents (e.g. antibiotics, NSAIDs, glaucoma medications, angiogenesis inhibitors, neuroprotective agents), cytotoxic agents, diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be associated with an elastomeric material disclosed herein to be released.

In some embodiments, agents for delivery utilized in accordance with the present disclosure are one or more therapeutic agents. Exemplary agents include, but are not limited to, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, drugs, vaccines, immunological agents, etc., and/or combinations thereof. In some embodiments, a therapeutic agent to be delivered is an agent useful in combating inflammation and/or infection.

In some embodiments, a therapeutic agent is a small molecule and/or organic compound with pharmaceutical activity. In some embodiments, a therapeutic agent is a clinically-used drug. In some embodiments, a therapeutic agent is or comprises an antibiotic, anti-viral agent, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

In some embodiments, a therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof.

An antibiotic used in accordance with the present disclosure may be bacteriocidial or bacteriostatic. Other antimicrobial agents may also be used in accordance with the present disclosure. For example, anti-viral agents, anti-protazoal agents, anti-parasitic agents, etc. may be of use.

In some embodiments, a therapeutic agent may be an anti-inflammatory agent. Anti-inflammatory agents may include corticosteroids (e.g., glucocorticoids), cycloplegics, non-steroidal anti-inflammatory drusg (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

Additionally or alternatively, an agent having NSAID-like activity can be used. Suitable compounds having NSAID activity include, but are non-limited to, the non-selective COX inhibitors, selective COX-2 inhibitors, selective COX-1 inhibitors, and COX-LOX inhibitors, as well as pharmaceutically acceptable salts, isomers, enantiomers, polymorphic crystal forms including the amorphous form, co-crystals, derivatives, prodrugs thereof.

Those skilled in the art will recognize that this is an exemplary, not comprehensive, list of agents that can be released using compositions and methods in accordance with the present disclosure. In addition to a therapeutic agent or alternatively, various other agents may be associated with elastomeric compositions and materials in accordance with the present disclosure.

Uses and Applications

In various embodiments, the present inventions provide biodegradable elastomeric compositions and materials tunable for use in many medical or non-medical applications. Exemplary applications described in U.S. Pat. No. 7,722,894 and U.S. Pat. No. 8,143,042 can be applicable in accordance with the present disclosure, the contents of both references are hereby incorporated by reference.

Fabrication of provided biodegradable elastomeric compositions and materials can be done prior to use. Additionally or alternatively, at least partial fabrication can be done in situ. For example, a precursor composition comprising a pre-polymer and a crosslink can be implanted and cured in vivo. In some embodiments, a precursor composition is injected. In some embodiments, a precursor composition is implanted or applied during surgery.

In some embodiments, elastomeric materials, in particular, those are transparent can be used in a form of contact lenses and/or patches on the surface of an eye. Such contact lenses can comprises ocular drugs for delivery. In some embodiments, transparent elastomeric materials can be part of a device transplanted into an eye to treat macular degeneration, diabetic retinopathy, glaucoma and/other eye diseases. For example, they can be part of a punctal plug.

In some embodiments, elastomeric materials, in particular, those are transparent can be used in a form of medical patches. Such patches can be attached to tissue using light activated adhesives (non-transparent materials cannot). If the procedure is done minimally invasive, it may be beneficial that a patch maintains its optically transparent properties after contact with body fluids. Such patches can be helpful for observation of underlying tissue after defect closure. For example, if a patch is used to close a stomach ulcer, an endoscopy can be done to see if the ulcer is closing properly.

Due to its elastomeric nature, the compositions and materials of the present inventions can be used in tissue engineering/reconstruction of tissues, especially muscle tissue, bladder, artery and heart valves. Additional or alternatively, elastomeric compositions and materials can be applied to other tissues such as lung, colon, tendon, ligament, dura, brain, etc. In certain embodiments, elastomeric compositions and materials are used as a bandage for skin or on other tissues.

For example, in various embodiments, an elastomeric composition or material of the present invention can be used in the form of tubes, e.g., for peripheral nerve reconstruction. Preferably, the tube is constructed to withstand pressure of the surrounding tissue and guide the nerve in its outgrowth, substantially unhampered by scar tissue formation. In peripheral nerve regeneration applications, it is preferred that the material be functionalized (e.g., with GRGD) to facilitate the attachment and guidance of Schwann cells.

For example, in various embodiments, a biodegradable elastomeric of the present invention can be used as a matrix, scaffold, or structure for cell attachment and/or encapsulation. In some embodiments, short-peptides (e.g., GRGD) can be incorporated into a biodegradable elastomeric material of the present invention to enhance cell adhesion. Incorporation of these short peptides can be achieved by mixing the functionalized peptides with a pre-polymer followed by crosslinking. For example, a GRGD peptide can be functionalized with a poly(ethylene glycol) spacers and a hydroxyl or amino group.

In various embodiments, the present inventions provide biodegradable elastomeric compositions and materials as a 3D matrix for encapsulation and proliferation of cells. For example, matrixes may be seeded with a variety of cells, such as, tenocytes, fibroblasts, ligament cells, endothelial cells, epithelial cells, muscle cells, nerve cells, kidney cells, bladder cells, intestinal cells, chondrocytes, bone-forming cells, stem cells such as human embryonic stem cells or mesenchymal stem cells, and others. In certain embodiments, matrixes are configured for stem cells.

Other medical applications may also benefit from elastomeric compositions and materials of the present invention. For example, after abdominal surgery, the intestines and other abdominal organs tend to adhere to one another and to the abdominal wall. It is thought that this adhesion results from post-surgical inflammation, however, anti-inflammatory drugs delivered directly to the abdominal region dissipate quickly. Elastomeric compositions and materials may be used to deliver anti-inflammatory drugs to the abdominal region. It may be implanted between the abdominal wall and internal organs, for example, by attaching it to the abdominal wall, without cutting internal organs, which would lead to infection. The anti-inflammatory drug can be released from elastomeric compositions and materials over a period of months. While previous researchers have attempted to use hydrogels, hyaluronic acid-based membranes, and other materials to solve these problems, such materials tend to degrade quickly in the body; a longer resident period is necessary to prevent adhesion.

Elastomeric compositions and materials may be used to coat any medical devices. In some embodiments, a medical device is an implantable device.

In some embodiments, an elastomeric composition or material can be used to coat a metallic stent. It may expand with the stent without ripping, while the stiffness of the metal stent will prevent the elastomeric composition or material from elastically assuming its previous shape. An elastomeric composition or material may release heparin or other anti-coagulants or anti-inflammatory agents to prevent the formation of clots or scar tissue, which could close off the blood vessel or throw off a thrombus that could cause circulatory problems, including stroke, elsewhere in the body. Alternatively or in addition, angiogenic agents may be used to promote the remodeling of the blood vessel surrounding the stent.

In some embodiments, an elastomeric composition or material may be used to prepare "long term" medical devices. Unlike typical permanent medical devices, an elastomeric composition or material will degrade over time. For example, an elastomeric composition or material may be fabricated into a biodegradable cardiac stent. In certain embodiments, an elastomeric composition or material is combined with a harder polymer that plastically forms for the production of stents. Exemplary polymers include any of the polymers known in the art, preferably biodegradable polymers. An elastomeric composition or material may act as a plasticizer that enables the stent to expand into the desired shape after implantation. The stent increases the diameter of the blood vessel to allow easier circulation, but, because the stent is biodegradable, surrounding blood vessels increase in diameter without thrombosis or covering the stent with scar tissue, which would reclose the blood vessel. The time the stent should remain in place and retain its shape before degradation will vary from patient to patient and depend partially on the amount of blockage and the age of the patient (e.g., older patients require more time to heal).

In some embodiments, an elastomeric composition or material can be used as surgical glue. A biocompatible, biodegradable surgical glue may be used to stop bleeding during surgery but does not need to be removed before the surgeon sutures the wound closed and will degrade over time.

In some embodiments, an elastomeric composition or material can be used as a patch for soft tissue defect repair (e.g. closure of defects, such as vascular defects, cardiac defects, GI defects).

In some embodiments, an elastomeric composition or material can be used to support in vivo sensors and catheters. It can be constructed into a chamber for an optical fiber-based sensor or a coating for a catheter that is inserted into the area of interest. In a sensor, the chamber contains a specific chromophore-bonded receptor for the molecule of interest. When an analyte attaches to the receptor, the chromophore will either emit or absorb light at an specific wavelength. The absorption or emission may be detected by an apparatus connected to the optical fiber. The sensor may be used for short term, continuous monitoring, for example, for ten to fifteen days. Likewise, a catheter may be used to periodically deliver drugs or other small molecules or bioactive agents to a specific site or intravenously. Use of an elastomeric composition or material reduces the formation of scar tissue which would ordinarily form around a shunt or other implant that is used for more than two weeks. The degradation rate of the bio-rubber should be optimized so that there is not significant degradation of the material while it is in place in the patient.

As discussed above, in some embodiments, an elastomeric composition or material comprises an agent for delivery. Such an elastomeric composition or material can be used in drug delivery. Hydroxyl or amino groups on an elastomeric composition or material of the present invention provide sites to which molecules may be attached to modify the bulk or surface properties of the material. For example, in various embodiments, tert-butyl, benzyl, or other hydrophobic groups can be added to the material to reduce the degradation rate. In various embodiments, polar organic groups such as methoxy can be used to facilitate adjustment of degradation rate and hydrophilicity. In various embodiments, addition of hydrophilic groups, for example, sugars, at these sites can be used to increase the degradation rate.

In various embodiments, acids can be added to an elastomeric composition or material described here to modify the properties of the material. For example, molecules with carboxylic or phosphoric acid groups or acidic sugars can be added. In various embodiments, charged groups such as sulfates and amines can be attached to elastomeric compositions and materials. Groups that are added to elastomeric compositions and materials can be added, for example, via linkage to a free hydroxyl/amino group (substituting for hydrogen), linked directly to the polymer backbone by substituting for a hydroxyl/amino group, incorporated into an organic group which is linked to elastomeric compositions and materials, and/or incorporated into a cross-link as part of the link or as a substituent on the link.

In various embodiments, attachment of such non-protein organic or inorganic groups to an elastomeric composition or material can be used to modify its hydrophilicity and the degradation rate and mechanism. In various embodiments, protecting group chemistry can be used to modify the hydrophilicity of the material.

In various embodiments, to, for example, facilitate controlling and/or regulating material interaction with cells; biomolecules and/or bioactive agents may be coupled to a hydroxyl/amino group or integrated into the polymer backbone. Association biomolecules and/or bioactive agents with elastomeric compositions and materials can be conducted in many ways known in the art. In some embodiments, biomolecules and/or bioactive agents are encapsulated within elastomeric compositions and materials. In some embodiments, biomolecules and/or bioactive agents are attached to elastomeric compositions and materials, e.g., covalently, non-covalently, etc. Such attachment can result in a slower release rate.

In various embodiments of compositions and materials of the present inventions including one or more biomolecules and/or bioactive agents, the cross-link density of one or more types of cross links is adjusted by adjusting the degree of urethanation, the proportion of one or more co-polymers, or both, to provide an elastomeric composition or material that has a desired biomolecule and/or bioactive agent release rate, release profile, or both.

In various embodiments, for example, biomolecules such as growth factors can be incorporated into a wound dressing/sealant comprising a composition or material of the present inventions to recruit cells to a wound site and/or promote specific metabolic and/or proliferative behavior in cells that are at the site and/or seeded within the matrix. Exemplary growth factors include, without limitation, TGF-β, acidic fibroblast growth factor, basic fibroblast growth factor, epidermal growth factor, IGF-I and II, vascular endothelial-derived growth factor, bone morphogenetic proteins, platelet-derived growth factor, heparin-binding growth factor, hematopoetic growth factor, and peptide growth factor. In various embodiments, integrins and cell adhesion sequences (e.g., the RGD sequence) can be attached to the compositions and materials of the present inventions to facilitate cell adhesion. In various embodiments, extracellular matrix components, e.g., collagen, fibronectin, laminin, elastin, etc., can be combined with compositions and materials of the present inventions to manipulate cell recruitment, migration, and metabolism and the degradation and mechanical properties of the material. In various embodiments, proteoglycans and glycosaminoglycans can be covalently or non-covalently attached to compositions and materials of the present inventions.

EXEMPLIFICATION

Aspects of the present disclosure may be further understood in light of the following examples, which are not exhaustive and which should not be construed as limiting the scope of the inventions described here in any way.

In the following examples, we describe a novel biocompatible and mechanically tunable elastomer, poly(glycerol sebacate urethane) (PGSU). Various elastomeric compositions and materials, in some embodiments, are suitable for efficient encapsulation and controlled delivery of bioactive macromolecules, and may be applied on cardiac drug delivery.

Example 1: PGS Pre-Polymer Synthesis

All chemicals were purchased form Sigma-Aldrich (Milwaukee, Wis.) and used as received unless otherwise specified. Poly(glycerol sebacate) (PGS) pre-polymer was synthesized through the polycondensation of equimolar amounts (0.05 mol) of glycerol and sebacic acid at 120° C. and under nitrogen atmosphere for 8 hours. The pressure was reduced using an in-house vacuum line and the reaction followed for 16 hours, yielding a pale-yellow viscous pre-polymer. The molecular weight was evaluated using gel permeation chromatography (Viscotek TDA 305 with Agilent 1260 pump and autosampler, Malvern Instruments, Worcestershire, United Kingdom). Samples were solubilized in tetrahydrofurane (THF) as solvent and eluted through a series of three columns (CLM3010 LT6000L, Malvern) at a flow rate of 1 ml/min. Linear polystyrene standards were used for calibration.

Example 2: Methodology for Preparing PGS Pre-Polymer with Different MWs

The present Example describes methodologies used to prepare exemplary PGS pre-polymers of different molecular weights.

PGS pre-polymer was synthesized through the polycondensation of equimolar amounts (0.05 mol) of glycerol and sebacic acid at 120° C. and under nitrogen atmosphere for 8 hours. The pressure was reduced using an in-house vacuum line and the reactions followed for:

<13 hours—for a molecular weight bellow 5,000 Da 16 hours—for a final molecular weight of around 10,000 Da 22 hours—for a final molecular weight about 20,000 Da It should be understood that the molecular weights indicated above are those usually observed in reactions under the indicated conditions, but as those skilled in the art variability can occur, for example due to variations in vacuum intensity or temperature control of the reaction.

It will further be understood that it is not always desirable or possible to make molecular weight measurements of all samples through GPC. However, reaction time can be controlled and viscous properties of produced pre-polymers can be evaluated. Viscous properties are known to correlate to molecular.

Example 3: PGSU Synthesis Using a Solvent-Based Approach (PGSU-S)

To synthesize PGS-urethane (PGSU), after cooling, the PGS pre-polymer was solubilized in dimethylformamide (DMF, 10% w/v) and heated to 55° C. in the presence of the catalyst stannous 2-ethyl-hexanoate (Tin (II), 0.05% w/v). Hexamethylene diisocyanate (HDI) was added dropwise to the reaction mixture. To obtain polymeric films with distinct physico-chemical properties, different molar ratios of HDI were used (glycerol:HDI-1:1, 1:0.5, 1:0.3). The reaction flask was purged with nitrogen, sealed and the reaction followed for 5 h. The solution was then cast on a teflon mold and the solvent allowed to evaporate for 3 days at room temperature and 2 days in a vacuum oven at 30° C. to obtain smooth, non-porous films. Solubility of PGSU-S films was evaluated in solvents including THF, dimethylsulfoxide, dioxane, DMF, dichloromethane.

Example 4: Properties of PGSU Films Prepared Using Solvent Based Methodology

The present Example describes the impact of various reaction conditions and components on certain mechanical properties of PGSU films prepared using solvent-based methodology as described herein.
A—Effect of Molecular Weight
A.1—Molecular Weight Profoundly Impacts Properties
For all the conditions, a constant amount of tin II catalyst (0.1% w/v) was used, and reactions were performed in 10% PGS (w/v) solutions. It was observed that a) low MW (below about 5000 Da) pre-polymers do not permit preparation of PGSU-S with a crosslinking degree of 1:0.3; higher crosslink ratios can be achieved; b) high MW (above about 20,000 Da) do not follow the standard reaction times, especially under conditions of high crosslinking degree (1:1) as it will gel in the flask and do not allow film casting; and c) films do not form with crosslinking ratios below 1:0.3 for the standard Mw of 10,000 Da.

Example 5: PGSU Synthesis Using a Solvent-Free Approach (PGSU-SF)

HDI pre-mixed with Tin(II) (1% v/v) was added to PGS pre-polymer and thoroughly mixed. Several ratios of crosslinking agent were tested (glycerol:HDI-1:1, 1:0.5, 1:0.3). To obtain thin non-porous films, immediately after homogenization, the mixture was spin coated (SCS G3 Spin Coater, Specialty Coating systems, Amherst, N.H.) at 3000 RPM for 3 minutes on glass coverslips. To facilitate ease of release from the underlying substrate, the coverslips surface was pre-modified with a (tridecafluoro-1,1,2,2-tetrahydrooctyl)-1-trichlorosilane (Gellest, Morrisville, Pa.). Briefly, after the first spin coating, the material was allowed to polymerize for at least 12 hours, followed by spin coating of a second layer directly on the already crosslinked film. The layered structure was confirmed by adding a fluorescent dye (rhodamin B and FITC) to each of the layers prior spin coating, followed by microscope observation. Elastomeric film thickness could be controlled by the consecutive layering of PGSU-SF or by changing the rotation speed during the spin coating procedure. Porous scaffolds were fabricated through a foaming process well known for polyurethane materials, without requiring the use of porogens or blowing agents. Briefly, HDI pre-mixed with Tin(II) (1% v/v) was thoroughly mixed with PGS pre-polymer, followed by casting on a Teflon mold containing grooves (1 cm in diameter and 1 mm in height). The presence of moisture, results in the reaction of HDI with water to form carbon dioxide gas, which diffuses through the elastomeric material and creates pores during the curing procedure. More details can be found in S. Guelcher, A. Srinivasan, A. Hafeman, K. Gallagher, J. Doctor, S. Khetan, S. McBride, J. Hollinger, *Tissue Eng.* 2007, 13, 2321, which is hereby incorporated by references.

Example 6: Properties of PGSU Films Prepared Using Solvent Free Methodology

The present Example describes the impact of various reaction conditions and components on certain mechanical properties of PGSU films prepared using solvent-free methodology as described herein. PGS having a MW of approximately 10,000 were used.
A. Effect of Catalyst
A.1—the Absence of Catalyst Results in Non-Elastic and Stiff PGSU Films
  PGSU-SF 1:0.3 prepared through mixing: PGS (100 mg)+HDI (23.8 mg)+Tin II (0.2 uL)
  PGSU-SF 1:0.3 prepared through mixing: PGS (100 mg)+HDI (23.8 mg)
  It was observed that a) patches prepared without Tin(ii) were very brittle and non-elastic; b) patches prepared with Tin(ii) were elastic and soft; and c) this was the minimum amount of catalyst tested throughout our experiments.
  A.2-Replacement of Tin (II) with DABCO Results in Non-Elastic Stiff PGSU Films
  PGSU-SF prepared through mixing: PGS+HDI (23.8 mg)+tin II (0.6 uL)
  PGSU-SF prepared through mixing: PGS+HDI (23.8 mg)+DABCO (0.6 uL)
  It was observed that a) PGSU patches prepared with tin (ii) were soft and elastic; and b) PGSU patches prepared with DABCO were brittle and non-elastic (similar to when no catalyst was used).
B—Effect of Crosslinker
B.1-Improved Curing with Crosslinker Ratio of at Least 1:0.3
  PGSU-SF 1:0.3 prepared through mixing: PGS (100 mg)+HDI (23.8 mg)+tin II (0.2 uL)
  PGSU-SF 1:0.2 prepared through mixing: PGS (100 mg)+HDI (15.8 mg)+tin II (0.13 uL)
  After mixing, the elastomeric materials were casted on a teflon surface (no spin coating) and crosslinking evaluated after 5 hours. It was observed that a) PGSU-SF 1:0.2 did not cure, while PGSU-SF 1:0.3 cured within a few hours.
C. Effect of Molecular Weight
C.1-Molecular Weight Below about 5000 does not Show Complete Film Curing
  Two PGS pre-polymers were tested and molecular weights were determined through GPC. PGS pre-polymer 1 shows Mw=3820; Mn=1684. PGS pre-polymer 2 shows Mw=3897; Mn=1594.

PGSU-SF 1:0.3 prepared through mixing: PGS (100 mg)+HDI (23.8 mg)+tin II (0.2 uL)

The crosslinking was evaluated after 24 hours. Neither of the two pre-polymers with low molecular weights allowed synthesizing films showing not enough crosslink.

C.2—High Molecular Weight PGS Pre-Polymer (>20 000) does not Form Uniform Thin Films We have synthesized several batches with Mw above 20,000 (e.g. Mw=23086, Mn=3068). We could not prepare uniform films using these pre-polymers, as these would gel before allowing easy spreading and spin coating of the material. Equivalent amounts of HDI and tin (II) (100 mg of PGS+23.8 mg of HDI+0.2 uL of tinII) were used as in previous experiments.

Example 7: Thermally Cured PGS Synthesis

Thermally cured PGS was synthesized as previously described. Briefly, the synthesized PGS pre-polymer was added to a Teflon mold and cured for 72 hours at 120° C. and under vacuum. The cured elastomeric material was carefully removed from the Teflon mold, extracted in absolute ethanol for 24 hours, dried and stored at −20° C. until further use. More experimental details can be found in Y. D. Wang, G. A. Ameer, B. J. Sheppard, R. Langer, *Nat. Biotechnol.* 2002, 20, 602, which is hereby incorporated by reference.

Example 8: PGSU Characterization and Discussion

Swelling Behavior and Sol Content of PGSU-S Films:

Dry polymer disks (4 mm in diameter and an average thickness of 0.3 mm, n=5) were weighed ($m_d$) and immersed in 5 mL of ethanol or PBS. After 24 hours, samples were removed and, gently wiped and weighed in the swollen state ($m_s$). Swelling percentage was determined according to the formula:

Swelling (%)=$[m_s-m_d)/m_d]\times100$

For sol content determination, samples (n=6 per condition) swollen in ethanol for 24 hours were dried in an oven at 50° C. until constant weight was achieved. Sol content was determined according to the formula:

Sol content (%)=$[(m_i-m_f)/m_i]\times100$

Attenuated Total Reflectance Fourier Transform Infrared Spectroscopy (ATR-FTIR):

ATR-FTIR was performed using a Bruker Alpha spectrophotometer (Billerica, Mass.) to determine the molecular structure of the PGS pre-polymer and PGSU films.

Differential Scanning Calorimetry of PGS-S Films:

Thermal properties of elastomeric films prepared through the solvent-based method were evaluated using a differential scanning calorimeter (Perkin Elmer Pyrisl, Waltham, Mass.): a first cycle was run between −50 and 100° C. to normalize the thermal history of all the samples, followed by a second cycle in the same temperature range performed at heating and cooling rates of 20° C./min and 40° C./min, respectively. Glass transition temperature ($T_g$) was measured as the midpoint of the heat-capacity change in the second heating cycle.

Mechanical Properties Evaluation:

Mechanical testing was performed on an ADMET eXpert 7601 universal tester (Norwood, Mass.), equipped with a 50N load cell with dog bone shaped specimens (5 mm×3 mm) with an approximate sample thickness of 0.2 mm PGSU-S samples were treated for 24 hours in ethanol to remove sol content. For PGSU-SF samples, sol content was not removed as we envision the application of this material for drug delivery applications, where this step would not be applicable. All samples were immersed in phosphate buffer saline (PBS) at 37° C. for 24 hours prior testing. Uniaxial tensile testing was performed at a jog rate of 50 mm/min until sample failure (n>4 per condition) and Young's modulus calculated as the slope at 15% strain. Results were compared to the previously described thermally cured PGS. Cyclical fatigue tensile testing (n=3) was performed at a jog rate of 50 mm/min, by sample extension until 30% elongation during 100 consecutive cycles.

In Vitro Degradation Studies of PGSU-S Films:

In vitro enzymatic degradation was evaluated using bovine pancreatic cholesterol esterase solution (40 U/mL) using weighted ($m_i$) dry PGSU discs (4 mm in diameter with an average thickness of 1 mm, n=3 per time point and condition). Enzyme solution was changed every 24 hours to ensure esterase activity. After each time point, discs were rinsed thoroughly with double distilled water and dried at 60° C. until constant weight ($m_f$). Remaining mass was calculated using the formula:

Remaining mass (%)=$[(m_f-m_i)/m_i]\times100$

In Vitro Biocompatibility of PGSU-S Films:

Human mesenchymal stem cells (hMSC) were cultured in α-MEM medium supplemented with 15% fetal bovine serum (Atlanta Biologics, Lawrenceville, Ga.), 1% (v/v) L-glutamine, 1% (v/v) penn-strep at 37° C. and 5% $CO_2$. For all experiments, cells between passage 3 and 6 were used. Glass coverslips with 15 mm diameter were cleaned with sodium hydroxide solution (10% w/v) followed by sonication with absolute ethanol, drying with nitrogen gas and activation with oxygen plasma (Harrick Plasma PDC-002, Ithaca, N.Y.) for 10 minutes. PGSU-S solutions (10% w/v) were immediately spin coated at 1500 RPMs and left to dry at 30° C. until constant weight. Prior to cell seeding, spin-coated cover slips were disinfected under UV for 1 hour, extracted with cell media for 3 hours, washed with PBS and placed into the wells of 24 well non-tissue culture treated plates. Tissue culture plastic (TCP) served as a positive control. Cells were seeded at a density of 2000 cells/$cm^2$ with 1 mL of growth media per well (n=3 per condition and time point). Media was changed after the first 24 hours and then every 3 days. At 1, 3, 6 and 8 days, metabolic activity was evaluated through an MTT assay (Invitrogen, Grand Island, N.Y.) performed according to the vendor protocol and the absorbance read at 570 nm using an Epoch microplate reader (BioTek, Winooski, Vt.). Prior to MTT, each well was rinsed with PBS and coated cover slips were transferred to new wells. At days 1 and 8, phase-contrast microscope pictures were acquired for both polymer and control (TCP) wells using a TE2000-U Inverted Nikon Microscope with a DS-Qil monochrome cooled digital camera.

In Vivo Biodegradation and Biocompatibility of PGSU-S Films:

All surgical procedures were approved by the Institutional Animal Care and Use Committee (IACUC) of the Massachusetts General Hospital and performed according to the NIH Guidelines for the Care and Use of Laboratory Animals. All experiments involved the subcutaneous implantation of polymer discs in adult female Lewis rats (Charles River Laboratories, Wilmington, Mass.). Specifically, three 1.5 cm long midline incisions were made on the back of each animal. Autoclaved and pre-wetted PGSU-S (1:1, 1:0.5, 1:0.3) discs with 10 mm diameter and an average thickness of 0.5 mm were implanted subcutaneously in random positions. As control, PLGA discs with similar dimensions (50:50 carboxylate end group, Durect Corporation) were used. At the predefined time points (1, 4, 8, 20, 40 weeks), the implants and surrounding tissue were harvested. For time points 1 and 4 weeks, three replicas per material and time point were implanted, while five replicas per material and per time were used for time points 4, 8, 20 and 40 weeks (n=2 for histology evaluation, n=3 for weight loss evaluation). Remaining dry disc weight was determined and compared with sample weight prior implantation. The microscale morphology of implants was evaluated through scanning electron microscopy (SEM, Jeol 5910). Tissue sections were prepared and stained with Hematoxylin and Eosin (H&E) and anti-CD68 stains.

In Vivo Cardiac Biocompatibility of PGSU-SF Films

All surgical procedures were approved by the IACUC of the Children's Hospital Boston and performed according to the NIH Guidelines for the Care and Use of Laboratory Animals. Briefly, adult male Wistar rats (Charles River Laboratories, Wilmington, Mass.) were anesthetized with an intraperitoneal injection of ketamine (100 mg/kg) and xylazine (10 mg/kg), followed by intratracheal intubation. Rats were ventilated with a small animal respirator (Harvard Apparatus, Holliston, Mass.), and anesthesia was maintained with 0.5 to 1.0% isofluorane and 100% oxygen. The heart was accessed through an anterior right-sided thoracotomy, followed by the removal of the pericardial sac. A 1 mm thick and 7 mm in diameter porous PGSU-SF 1:0.3 patch was sutured on the left ventricle (LV) epicardial surface of the rat heart using three 7-0 polypropylene monofilament stitches. The chest wall was closed in layers, and the thoracic cavity evacuated with a 18-gauge intravenous catheter. Animals were sacrificed at 1 and 4 weeks (n=4 per time point) after the surgical procedure with $CO_2$, followed by immediate excision of the heart. Tissue sections transverse to the patch and heart surface were stained with Hematoxylin and Eosin stain (H&E). Echocardiographic analysis (VIVID7, GE Medical Systems, equipped with a 15 MHz probe) was performed prior to surgical procedures and immediately before animal sacrifice to access cardiac function.

Protein Delivery Studies:

The incorporation of bioactive molecules in the PGSU elastomeric material was achieved by mixing the lyophilized proteins with PGS pre-polymer, followed by the addition of HDI and Tin(II) as previously described. For protein bioactivity studies, Lysozyme from chicken egg white (14.3 kDa) was used as a model protein with. Polymer discs with encapsulated protein (5 mg per 1 g of PGS pre-polymer) were immersed in 0.5 mL of PBS and incubated at 37° C. (n=4 per time point and condition). At defined time points the release supernatant was removed and stored at −20° C. until further analysis. The protein release profile was evaluated using a micro-BCA (Pierce, Rockford, Ill.) assay and the amount of active protein released was evaluated by monitoring the optical density changes of a *Micrococcus lysodeikticus* lysate solution, according to the vendor's protocol. For the controlled release studies, bovine serum albumin (BSA, 66.5 kDa, Millipore, Billerica, Mass.) was used. BSA only, or BSA co-lyophilized with trehalose (BSA:Tre, 1:1 mass ratio) were used in this study. Prior to encapsulation, BSA or BSA:Tre powders were sieved through 32 and 75 µm pores, to achieve a uniformly sized powder. The ratio of 34 mg of BSA or BSA:Tre to 100 mg of pre-polymer was constant throughout the study. Layers of non-porous PGSU-SF were spin coated. As a proof of concept, a three-layer strategy was used, while alternating the layer(s) where BSA or BSA:Tre was encapsulated. The same release and supernatant storage strategies were used for this study (n=3 per condition and time point). Differences in the release profile were evaluated through protein quantification using a micro-BCA assay.

Swelling Studies of PGSU-SF Films

Swelling studies were performed for trilayered PGSU-SF 1:0.3 films and PGSU-SF containing BSA or BSA-trehalose (1:1) in all the three layers. Loading was 34 mg per 100 mg of PGS for both conditions. Polymer disks (6 mm in diameter and an average thickness of 0.1 mm, n=3 per condition) were immersed in 5 mL of PBS. After 24 hours, samples were removed, gently wiped and weighed in the swollen state ($m_s$). Swollen samples were dried at 50° C. until constant weight ($m_d$). Swelling percentage was calculated relatively to dry mass after swelling according with the previously described formula.

Statistics

All the experiments were repeated at least three times and the average value was reported. Data are expressed as means±standard deviation. Statistical analysis was performed using one-way ANOVA with post hoc Tukey testing to examine statistical difference. Data were taken to be significant when a P-value of 0.05 or less was obtained.

Figure 6:
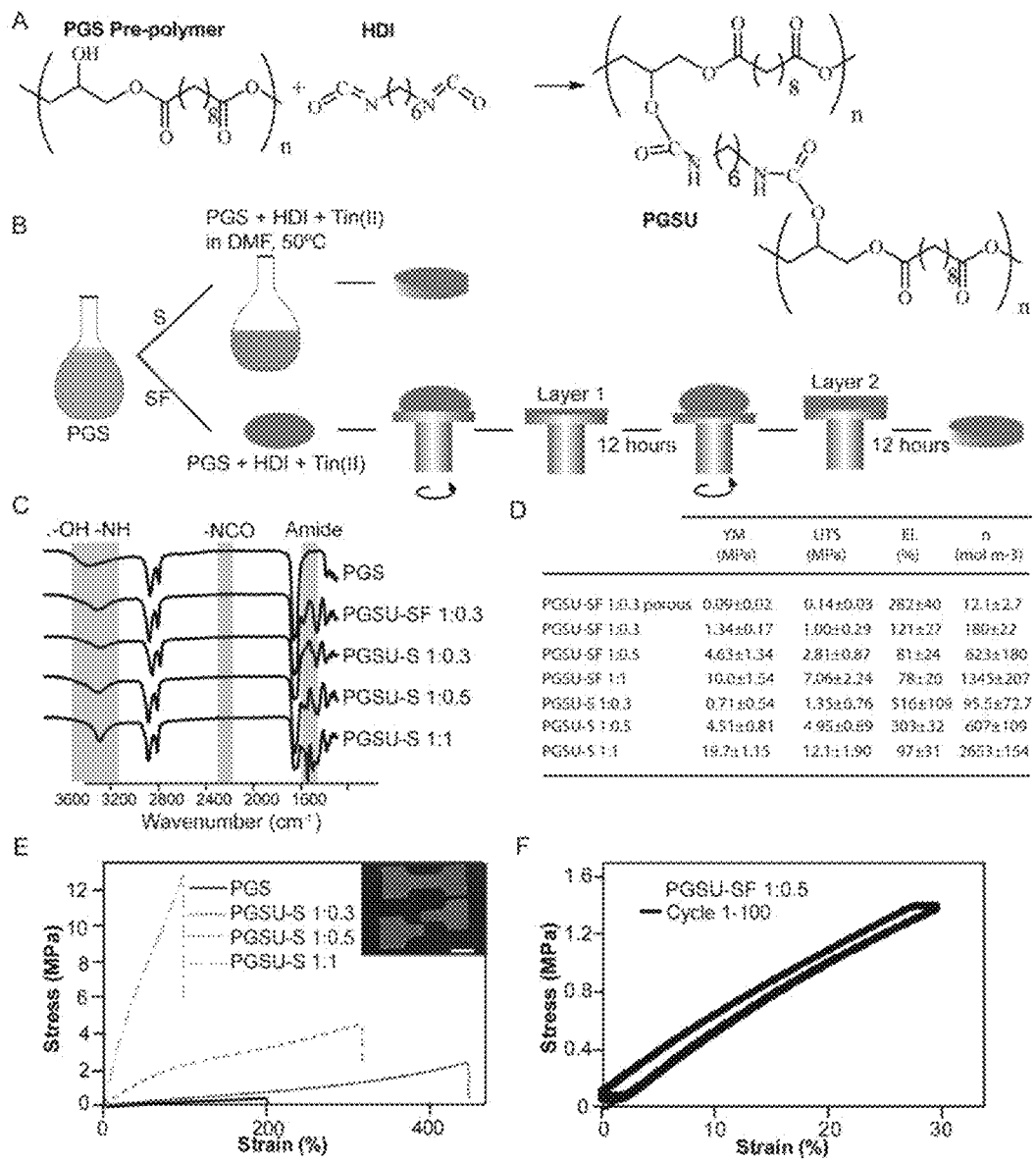
FIG. 6 shows chemical and mechanical characterization of exemplary PGSU elastomers. A) Synthetic scheme for PGSU. B) Schemes on solvent-based (S) and solvent-free (SF) routes to synthesize PGSU materials. C) FTIR analysis of PGS pre-polymer and PGSU elastomeric materials synthesized under solvent-based and solvent free conditions. D) Summary of mechanical properties and crosslinking degree of several PGSU derivatives. E) Typical stress-strain of PGSU-S films and thermally cured PGS elastomer and representative images of PGSU-S 1:0.5 films before and after tensile testing that reveal minimal deformation. F) Stress-strain profile of PGSU-SF 1:0.5 films under cyclical tensile loads, the elastomer is able to maintain its tensile properties with minimal creep after 100 cycles.

The PGS pre-polymer used in this study had a weight-average molecular weight of 12700±1600 g/mol and a polydispersity index of 4.5±0.5, as evaluated through gel permeation chromatography. Aliphatic hexamethylenediisocyanate (HDI) was chosen as the crosslinker given its low cost and wide use in the synthesis of biodegradable and biocompatible polyurethanes. Importantly, PGSU can be synthesized from these components through solvent-based (PGSU-S) and solvent-free (PGSU-SF) methods (FIG. 6B). In the solvent-based approach the reaction occurs in an organic solvent, followed by solvent casting. After evaporation, uniform non-porous films with transparent optical properties (FIG. 1A) are obtained. To achieve a non-porous elastomer synthesized under solvent-free conditions, after mixing PGS pre-polymer with the crosslinker, the mixture was spin-coated to achieve a uniform film (FIG. 1B) with thickness dependent on the spin coating rate. Several stacked layers can be subsequently spin-coated. A strong entanglement between layers is likely achieved due to the reaction of HDI with unreacted hydroxyl groups present in the underlying polymer layer. Porous scaffolds were also fabricated in the absence of organic solvents through a foaming process, well-known for polyurethanes. The presence of moisture results in the reaction of HDI with water to form carbon dioxide gas, which diffuses through the elastomeric material and creates pores during the curing process in thicker films (FIG. 1C). The PGS pre-polymer characteristics dictate the properties of the PGSU-SF films obtained: the presence of free hydroxyl groups in the pre-polymer backbone can be easily crosslinked under mild conditions, while the low viscosity at temperatures below 37° C. permits uniform mixing with HDI and spin coating to achieve uniform PGSU layers with controllable thickness. PGSU-SF films can be synthesized in under 24 hours, which is a major advantage compared to other elastomers that require long periods of time for complete polymerization or solvent evaporation.

The reaction efficiency and the molecular structure of the derivatives obtained were evaluated by FTIR (FIG. 6C). The PGS pre-polymer presents a broad peak at 3445 $cm^{-1}$, resulting from free hydroxyl groups (−OH stretch). With the addition of HDI, free hydroxyl groups are replaced by urethane groups and consequently a proportional deviation of this peak to lower wavelength (PGSU-S 1:0.3 at 3359 cm$^{-1}$, PGSU-S 1:0.5 at 3337 cm$^{-1}$, PGSU-S 1:1 at 3329 cm$^{-1}$) is observed, corresponding to the —NH group stretch. This shift also reveals the increase in hydrogen bonding forces with the isocyanate linker content. The peak near 1735 cm$^{-1}$ is attributed to the carbonyl group stretching from ester groups in PGS pre-polymer and PGSU derivatives. Amide I and amide II bands at 1630 and 1580 cm$^{-1}$ are only observed in PGSU derivatives, further confirming the establishment of urethane linkages in the polymer backbone. The absence of the characteristic isocyanate group band at 2270 cm$^{-1}$ reveals the complete reaction of the isocyanate groups in all PGSU derivatives. Similar spectra were obtained for films prepared through the solvent-free approach, indicating no major chemical differences in the polymeric network established. All derivatives synthesized were insoluble in a variety of organic solvents (e.g. tetrahydrofuran, dimethylsulfoxide, dioxane, DMF, dichloromethane), further confirming the establishment of an interchain chemically crosslinked network.

Figure 2:
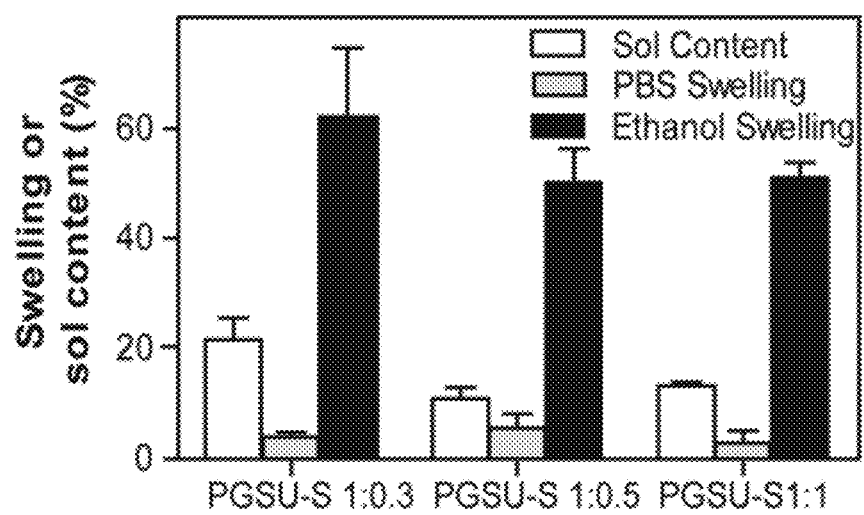
FIG. 2 demonstrates swelling properties of certain PGSU-S derivatives in PBS (37° C., 24 hours) and ethanol (RT, 24 hours), and respective sol content determined after ethanol extraction.

Thermal properties were evaluated for PGSU-S films, with all derivatives showing glass transition temperature ($T_g$) values below 0° C. (−11.8° C. for PGSU-S 1:0.3, −7.3° C. for PGSU-S 1:0.5, −4.2° C. for PGSU-S 1:1). The material's amorphous nature at room and body temperature assures it elastomeric properties. In addition, the lack of significative swelling of PGSU films in physiological solutions (FIG. 2) also contributes to its mechanical integrity once exposed to a wet environment (e.g. in vivo). The high degree of swelling in ethanol (FIG. 2) facilitates the removal of any unreacted monomers (sol content) entangled in the crosslinked network.

Several strategies have been previously reported to improve the mechanical properties of PGS elastomers, including the addition of micron-size fillers (e.g. Bioglass), or the introduction of novel functional groups (e.g. amide groups) to improve the polymer crosslinking. Despite considerable improvements in the range of properties achieved, high curing temperatures are still required. Through simply changing the degree of crosslinking introduces by the urethane groups, PGSU films can be tailored to achieve a broad range of mechanical properties (Young's modulus from 0.1 to 20 MPa, approximately), mimicking the stiffness of a diverse range of tissues, such as the myocardium, pericardium, skin, aorta, or cartilage (FIGS. 6C and D). Also of interest is the improved tensile strength of PGSU films compared to thermally cured PGS. For example, both PGSU-S and —SF 1:0.3 and PGS show a Young's modulus bellow 1 MPa but, the urethane crosslink improves the tensile strength (1.35±0.76 MPa for PGSU-S 1:0.3, 0.38±0.06 MPa for PGS) and elongation (516±109% for PGSU-S 1:0.3, 200±30% for PGS) properties of the material. These features may be exploited in load-bearing applications where strength and elasticity are essential. Furthermore, biomaterials are often significantly manipulated prior to proper placement and thus must maintain their integrity not only following transplantation but also during surgical implantation. Towards this end, PGSU also shows a favorable behavior when exposed to continuous cyclical loadings, presenting minimal creep deformation and minimal loss of tensile strength after 100 tensile cycles (FIG. 6F). The presence of covalent crosslinks between the polymeric chains likely prevents them from sliding past one another, therefore improving their stability under dynamic environments. In comparison, aliphatic polyurethanes have been associated with permanent deformation once exposed to tensile forces.

Figure 3:
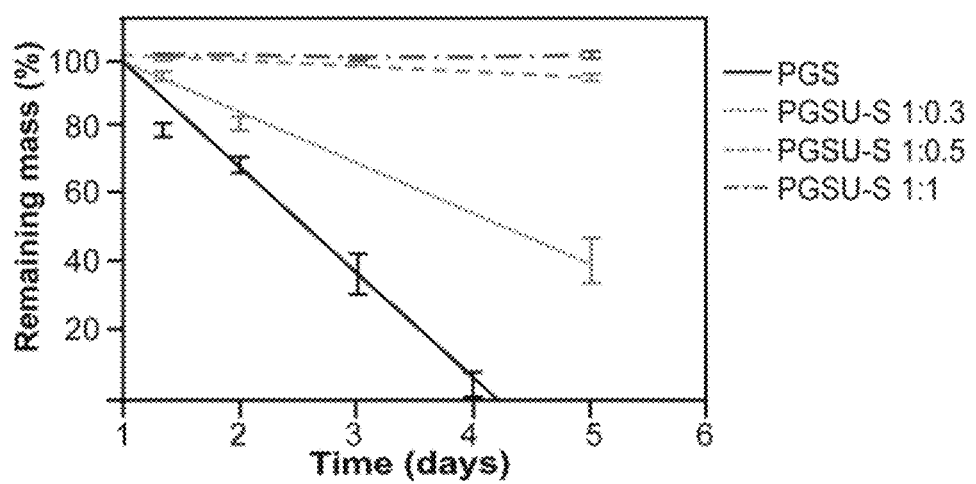
FIG. 3 shows in vitro degradations profile of certain PGSU-S discs (4 mm in diameter with an average thickness of 1 mm) and comparison with thermally cured PGS. Since enzymatic degradation may be the main degradation mechanism of polyester-based polymers, these studies were performed in a cholesterol esterase solution (40 UN/mL) at 37° C. The degradation rate of PGSU-S derivative is observed to be considerably lower than thermally cured PGS and dependent on the urethane content.
Figure 4:
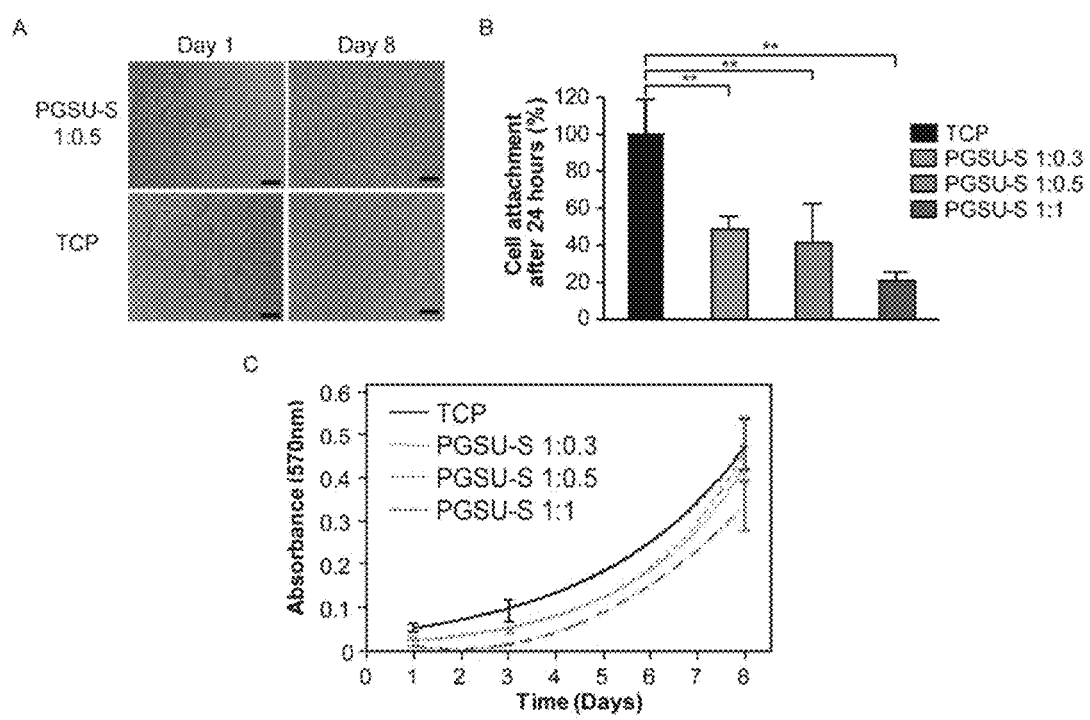
FIG. 4 demonstrates in vitro biocompatibility of PGSU-S films. A) Comparison of hMSC morphology when seeded in tissue culture polystyrene (TCP) and PGSU-S 1:0.5 at day 1 and day 8. The scale bar is 10 μm. B) Percentage of adherent cells at 24 hours after cell seeding. C) Proliferation kinetics for hMSC in PGS-U films and comparison when seeded on TCP, measured using an MTT assay.
Figure 7:
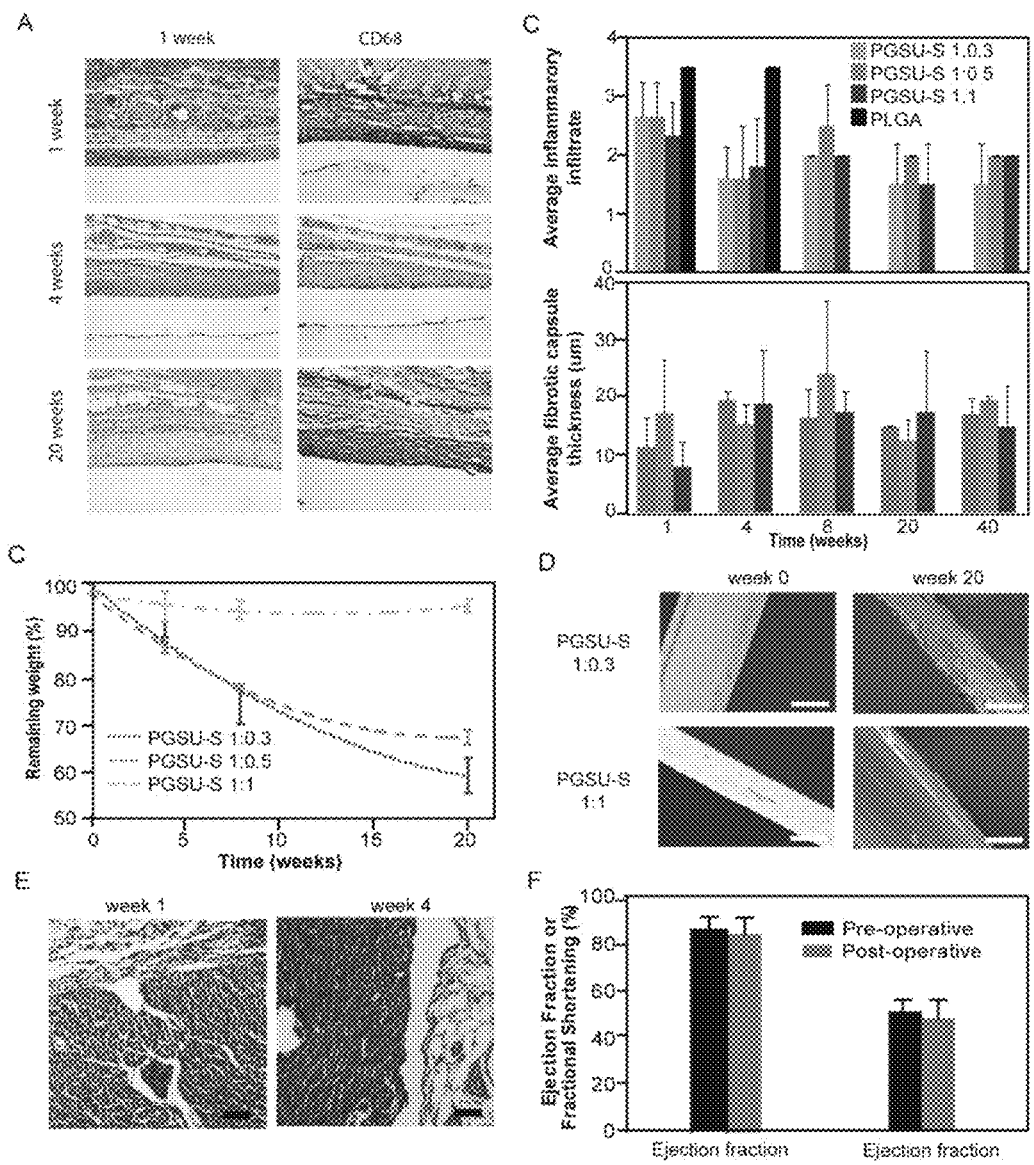
FIG. 7 demonstrates in vivo subcutaneous and cardiac biocompatibility and biodegradation of representative PGSU elastomers. A) Representative images of H&E and anti-CD68 stainings of the subcutaneous tissue surrounding PGSU-S elastomeric materials. Bars represent 200 μm B) Characterization of foreign body response to PGSU-S and PLGA implants through trough qualitative evaluation of the inflammatory infiltrate (classification: from 0 representing no infiltrate and 4 severe infiltrate). C) Subcutaneous in vivo degradation profile of PGSU-S films. D) Morphologic evaluation of PGSU-S cross-sections through SEM. Scale bars represent 50 μm. E) Representative images of H&E sections of cardiac tissue in contact with PGSU-SF 1:0.3 elastomer for 1 and 4 weeks. D) Cardiac function before and 4 weeks after PGSU-SF implantation.

To determine the potential of PGSU derivatives in biomedical applications, we assessed their biodegradation profiles and cytocompatibility in vitro. In the presence of cholesterol esterase, PGSU-S films exhibited a degradation profile dependent on the degree of crosslinking (FIG. 3). The ester groups in the polymer backbone are highly sensitive to enzymatic degradation; however, with increased urethane content the accessibility to ester bonds is hindered resulting in slower degradation rates. Human mesenchymal stem cells were used to test the cytocompatibility of PGSU-S materials. Cells adhered to PGSU-S films at lower extent than tissue culture polystyrene (TCP) (day 1); however, they were able to proliferate and at day 8 their metabolism, as assessed by a MTT assay, was not statistical different in both culture conditions (FIG. 4). Given the positive preliminary data, we examined the in vivo acute and chronic inflammatory response in a subcutaneous rat animal model and compared with poly(lactic-co-glycolic acid) (PLGA), an FDA-approved material for several internal applications. PLGA samples were only visible during harvesting at 1 week, as all samples were nearly fully degraded at 4 week post-implantation. No adverse reactions to the implants or complications were noted during the implantation period. H&E and anti-CD68 macrophage stainings were employed to characterize the inflammatory response to the implantes (FIG. 7A). The inflammatory responses to the PGSU-S was similar when comparing all derivatives, and characterized as mixed lymphohistiocytic reaction with predominance of histiocytic at 1 and 4 week time points and lymphocytic reaction at all later time points. No giant cells could be identified in any material group at any time point. All PGSU sample groups exhibited mild to moderate infiltration by CD68-positive macrophages at 1 wk post implantation; at all later time points, CD68-positive infiltration was characterized as mostly minimal. The inflammatory reaction to PLGA was significantly higher (p<0.5) at 1 and 4 weeks than the reaction to the PGSU-S (FIG. 7B). Capsule thickness did not vary significantly among all samples (FIG. 7B), and was considerably thinner when comparing with other previously described elastomers.

Following 20 weeks of implantation, all samples maintained their circular shape, with PGSU-S 1:0.3 and 0.5 exhibiting a gradual decrease in sample diameter and thickness, with a remaining weight of 59.9±3.9 and 68.2±1.5%, respectively (FIG. 7C). At week 40, explanted PGSU-S 1:0.3 and PGSU-S 1:0.5 samples were broken and therefore not considered for weight loss evaluation. The degradation rate observed for all the derivatives is slower than what has been described for other elastomers, such as PGS whose degradation rate cannot be tuned. SEM evaluation of PGSU-S 1:0.3 following 20 weeks showed minimal morphological changes on the micron-scale suggesting that the degradation mechanism is based on surface erosion (FIG. 6D). No significant weight loss or morphologic changes were observed for PGSU-S 1:1 samples during the 40 week study.

One of the areas where biodegradable elastomers are gaining much attention is cardiac therapy, with potential applications ranging from reconstructive procedures, tissue engineering to localized drug delivery. Previous studies demonstrated that the mechanical compliance and degradation properties of biomaterials applied to the heart strongly influence cardiac function and the material's integration with the host tissue. However, clinically-used materials (e.g., Dacron) are stiff, non-degradable and are associated with long-term fibrosis and calcification, compromising regional function. Porous PGSU-SF 1:0.3 exhibits similar mechanical properties to native heart tissue and, given the mild synthetic conditions, may allow localized delivery of bioactive macromolecules. Such an approach may provide new therapeutic options for cardiac disease given that many biomolecules exhibit short half-lives and/or present systemic toxicity. Towards potential cardiac applications, we performed a preliminary in vivo biocompatibility study to evaluate how porous PGSU-SF 1:0.3 interacts with myocardial tissue. Specifically, PGSU-SF films could be easily manipulated and sutured, showing excellent tear-resistant properties. Cardiac acute and chronic inflammatory responses to PGSU-S 1:0.3 films were evaluated one and four week after surgery, respectively, through H&E staining (FIG. 6E). While diffuse granulation tissue and infiltrated lymphocytes were visible surrounding the implant, the myocardial surface did not show signs of a significant inflammatory response and no major fibrotic response or collagen deposition was observed. No changes in cardiac function were observed via echocardiography analysis (FIG. 6F). Moderate chest adhesions, common following thoracotomy procedures, were observed during heart excision at both time points.

Given the possibility of preparing PGSU-SF elastomers under mild conditions, we evaluated its applicability as a controlled delivery system of bioactive molecules. While the use of polyurethane foams for the delivery of therapeutic proteins has been previously reported, the mechanical properties of the materials obtained have been limited to tensile moduli bellow 0.12 MPa. In contrast, proteins could easily be loaded directly into the highly tunable PGSU-SF, without interfering with the curing process or final properties of the elastomer. To evaluate the bioactivity of the released biomolecules, lysozyme was used as a model protein, given the availability of simple and cost-effective assays to quantify its activity. The protein was encapsulated in porous PGSU-SF and exhibited a small burst during the first 48 hours, followed by sustained protein release for at least 5 days (data not shown). Importantly, the majority of the protein released was bioactive (FIG. 8A).

Figure 5:
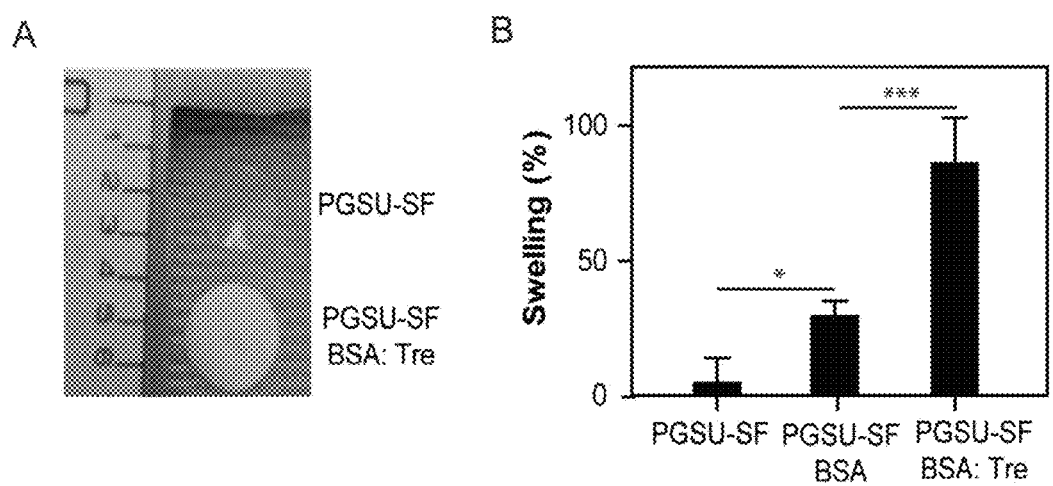
FIG. 5 shows swelling studies of PGSU-SF, and PGSU-SF with BSA or BSA-trehalose (1:1) encapsulated. A) Macroscopic appearance of films after 24 hours in PBS. B) 24 hour swelling ratio as percentage of sample dry weight. The co-encapsulation of BSA with trehalose improves the water uptake of exemplary PGSU-SF films.
Figure 8:
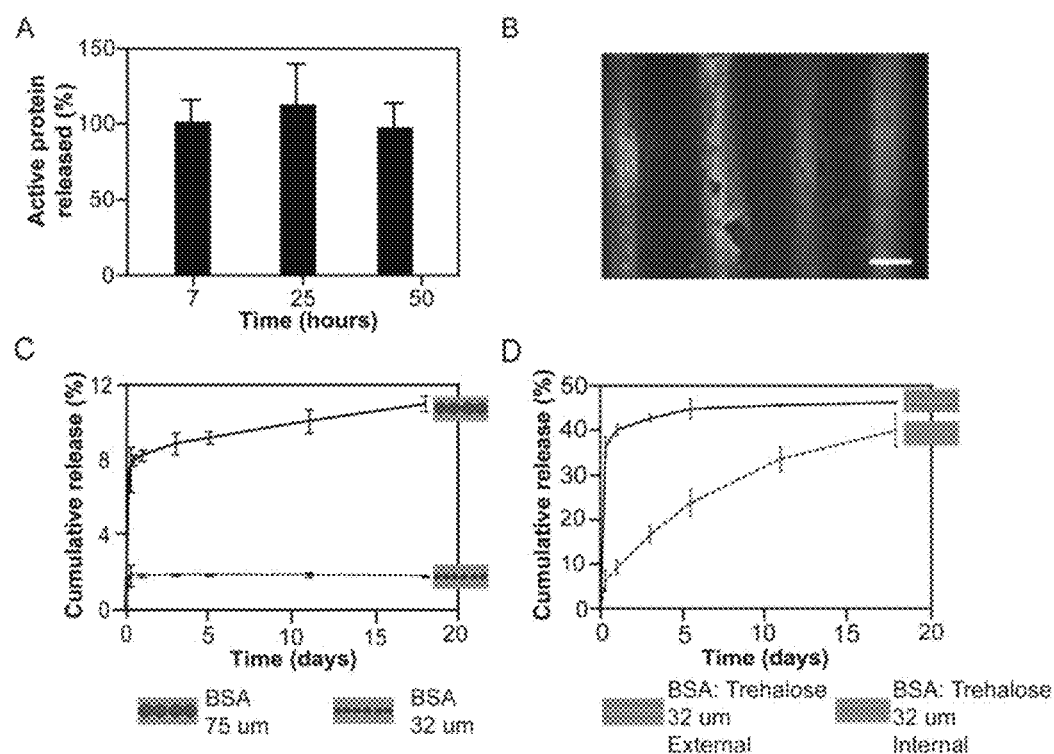
FIG. 8 illustrates sustained release of bioactive proteins from PGSU-SF films. A) Bioactivity of the lysozyme released from PGSU-SF porous patches. B) Selective encapsulation of rhodamin and FITC on intercalated PGSU layers using spin coating technique. Scale bars represent 20 µm. C) Release kinetics of the model protein BSA sieved to 75 and 32 µm particle size encapsulated on the internal layer of a trilayer spin-coated PGSU-SF 1:0.3 film. D) Release kinetics of the model protein BSA co-encapsulated with trehalose (1:1 ratio) and sieved to 32 um particle size from internal and externals layers of a trilayer spin-coated PGSU-SF 1:0.3 film.

Next, to achieve tighter control over the delivery profile, we developed a strategy based on the sequential layering of PGSU-SF, allowing fine control over the localization of the encapsulated molecules (FIG. 8B). When the pre-polymer is spin coated at 3000 RPM and without protein powder, the size of each layer is 33.5±0.1 µm. Given that the release is based on diffusion and polymer degradation mechanisms, controlled release could be achieved through altering the stacking order of protein-loaded and unloaded layers, the size of the encapsulated protein powder, and the presence of osmotic agents. As proof of concept, the lyophilized model protein Bovine Serum Protein (BSA) was sieved to particle sizes bellow 32 µm, similar to the thickness of each layer, and 75 µm. These were encapsulated in internal layers of PGSU-SF 1:0.3 films. Given the low swelling in aqueous solution of PGSU films, the majority of the protein is entrapped in the polymeric network, especially when the particle size is smaller than the layer thickness (FIG. 8C). The use of particles of bigger size results in increased protein release at earlier time points given the proximity to the polymer surface. This might promote a porous structure that further contributes the sustained release of protein for longer periods of time. The release efficiency could be improved through the co-encapsulation of BSA with an osmotic agent, trehalose, by improving the water uptake from PGSU-SF films (FIG. 5). The encapsulation of BSA-trehalose sieved to small particle size in internal PGSU-SF layers resulted with sustained protein release for more than 18 days, with almost 50% of the total loading released (FIG. 8D). The encapsulation of the same formulation in external polymer layers results in faster release of the protein loaded. These preliminary results demonstrate the versatility of PGSU-SF materials, which can be selectively modulated to achieve highly specific release kinetics through simple changes in the films preparation methods.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A composition comprising:
a polyester material, the material comprising a plurality of A and B components, wherein the A and B components form a plurality of polymeric backbones formed of (-A-B—) repeat units, having a general formula (-A-B—)$_p$, wherein:
p is an integer greater than 1;
the (-A-B—) repeat units have a chemical structure achieved when a polyol component A' is condensed with a polyacid component B';
at least two of the (-A-B—) repeat units within each of the polymeric backbones have at least one free hydroxyl group present thereon on the A component of the at least two (-A-B—) repeat units within the polymeric backbones;
wherein the polyester material has a molecular weight of between about 3,000 and about 50,000 Daltons; and
a polyisocyanate crosslinker;
wherein the at least one free hydroxyl group to the polyisocyanate crosslinker is present at a molar ratio of between 1:0.3 and 1:0.8;
wherein the polyester material crosslinked by the polyisocyanate crosslinker is an elastomeric polyester material cross-linked by a plurality of urethane crosslinks which covalently link the polymeric backbones at the A components of the at least two (-A-B—) repeat units; and
wherein the elastomeric polyester material crosslinked by the plurality of urethane crosslinks has one or more properties selected from the group consisting of:
the elastomeric polyester material as a non-porous film with the thickness of 200 µm transmits more than 75% of incident light;
the elastomeric polyester material has a Young's modulus of between about 0.5 MPa and about 30 MPa;
the elastomeric polyester material has a tensile strength of between about 0.5 MPa and about 15 MPa;
the elastomeric polyester material elongation of between about 50% and about 600%;
the elastomeric polyester material has a size deformation of below about 20% of its initial length, after tensile loading;
the elastomeric polyester material has tensile strength stable within about 5% to about 30% of the initial strength over 100 cycles of extension;
the elastomeric polyester material has a size deformation stable within about 5% to about 30% of the initial length over 100 cycles of extension; and combinations thereof.

2. The composition of claim 1, wherein the polyester material is non-linear.

3. The composition of claim 1, wherein the polyester material has a molecular weight between about 3,000 and about 25,000 Daltons.

4. The composition of claim 1, further comprising a catalyst.

5. The composition of claim 1, further comprising a solvent.

6. The composition of claim 1, further comprising a porogen.

7. The composition of claim 1, wherein the polyester material has a molecular weight between about 3,000 and about 20,000 Daltons.

8. An elastomeric cross-linked polyester material comprising:
   a plurality of A and B components, wherein the A and B components form a plurality of polymeric backbones formed of (-A-B—) repeat units, having the general formula (-A-B—)$_p$, wherein:
   p is an integer greater than 1;
   the (-A-B—) repeat units have a chemical structure produced by condensation of a polyol component A' with a polyacid component B';
   wherein the A component of at least two of the (-A-B—) repeat units within each of the polymeric backbones has at least one free hydroxyl group present thereon, prior to crosslinking;
   wherein crosslinking is carried out by a polyisocyanate crosslinker and the at least one free hydroxyl group to the polyisocyanate crosslinker at a molar ratio of between 1:03 and 1:0.8;
   wherein urethane cross-links covalently crosslink the polymeric backbones between the A components of the at least two (-A-B—) repeat units within each of the polymeric backbones;
   wherein the elastomeric cross-linked polyester material is a non-porous film having a thickness of 200 μm which transmits more than 75% of incident light; and
   wherein the elastomeric cross-linked polyester material has one or more properties selected from the group consisting of:
      a Young's modulus of between about 0.5 MPa and about 30 MPa;
      a tensile strength of between about 0.5 MPa and about 15 MPa;
      an elongation of between about 50% and about 600%;
      a size deformation of below about 20% of its initial length, after tensile loading;
      a tensile strength stable within about 5% to about 30% of the initial strength over 100 cycles of extension;
      a size deformation stable within about 5% to about 30% of the initial length over 100 cycles of extension; and
      combinations thereof.

9. The elastomeric cross-linked polyester material of claim 8, wherein the elastomeric cross-linked polyester material as the non-porous film with the thickness of 200 μm transmits more than 80% of incident light.

10. The elastomeric cross-linked polyester material of claim 8 in the form of a patch.

11. A method of making the elastomeric cross-linked polyester material of claim 8 comprising:
   providing a polyester material, the material comprising a plurality of A and B components, wherein the A and B components form a plurality of polymeric backbones formed of (-A-B—) repeat units having the general formula (-A-B—)$_p$, wherein:
   p is an integer greater than 1;
   the (-A-B—) repeat units have a chemical structure formed when a polyol component A' is condensed with a polyacid component B';
   at least two of the (-A-B—) repeat units within each of the polymeric backbones have at least one free hydroxyl group present thereon on the A component of the at least two (-A-B—) repeat units within the polymeric backbones;
   wherein the polyester material has a molecular weight between about 3,000 and about 50,000 Daltons; and
   mixing the polyester material with a polyisocyanate crosslinker,
   wherein the at least one free hydroxyl group to the polyisocyanate crosslinker is at a molar ratio of between 1:0.3 and 1:0.8, such that the elastomeric urethane cross-linked polyester material comprising a plurality of urethane crosslinks is produced,
   wherein the urethane crosslinks covalently crosslink the polymeric backbones between the A components of the at least two (-A-B—) repeat units within each of the polymeric backbones.

12. The method of claim 11, wherein the step of mixing is conducted in the presence of at least one solvent.

13. The method of claim 12, wherein the step of mixing is conducted at a temperature less than 45° C.

14. The method of claim 11, wherein the step of mixing is conducted in the absence of any solvent.

15. The method of claim 14, wherein the step of mixing is conducted at room temperature.

16. The method of claim 14, comprising mixing the polyester material with the polyisocyanate crosslinker, and implanting the mixture in an individual.

17. The method of claim 11, wherein the polyester material has a molecular weight between about 3,000 and about 25,000 Daltons.

18. The method of claim 11, further comprising a step of providing a catalyst.

19. The method of claim 11, wherein all steps are performed within 12 hours, 24 hours, or 48 hours.

20. The method of claim 11, wherein the polyester material has a molecular weight between about 3,000 and about 20,000 Daltons.

* * * * *